United States Patent
Cui et al.

(10) Patent No.: US 9,206,404 B2
(45) Date of Patent: Dec. 8, 2015

(54) METHOD OF DELETING AN IGM GENE IN AN ISOLATED RAT CELL

(75) Inventors: Xiaoxia Cui, St. Louis, MO (US); Aron M. Geurts, New Berlin, WI (US); Fyodor Urnov, Point Richmond, CA (US)

(73) Assignees: Sangamo BioSciences, Inc., Richmond, CA (US); Sigma-Aldrich Co. LLC, St. Louis, MO (US)

( * ) Notice: Subject to any disclaimer, the term of this patent is extended or adjusted under 35 U.S.C. 154(b) by 0 days.

(21) Appl. No.: 12/592,852

(22) Filed: Dec. 3, 2009

(65) Prior Publication Data

US 2010/0218264 A1 Aug. 26, 2010

Related U.S. Application Data

(60) Provisional application No. 61/200,985, filed on Dec. 4, 2008, provisional application No. 61/205,970, filed on Jan. 26, 2009, provisional application No. 61/263,904, filed on Nov. 24, 2009.

(51) Int. Cl.
*C12N 15/00* (2006.01)
*C12N 9/22* (2006.01)
*A01K 67/027* (2006.01)
*C12N 15/85* (2006.01)

(52) U.S. Cl.
CPC .............. *C12N 9/22* (2013.01); *A01K 67/0275* (2013.01); *A01K 67/0276* (2013.01); *A01K 67/0278* (2013.01); *C12N 15/8509* (2013.01); *A01K 2217/054* (2013.01); *A01K 2217/15* (2013.01); *A01K 2227/10* (2013.01); *A01K 2227/105* (2013.01); *A01K 2267/03* (2013.01); *A01K 2267/0393* (2013.01); *C07K 2319/00* (2013.01); *C07K 2319/81* (2013.01); *C12N 2800/80* (2013.01)

(58) Field of Classification Search
USPC .............................. 435/325; 800/8, 21, 14, 18
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 6,903,185 B2 | 6/2005 | Kim et al. | |
| 7,153,949 B2 | 12/2006 | Kim et al. | |
| 8,703,485 B2* | 4/2014 | Buelow ...................... 435/325 |
| 2003/0232410 A1* | 12/2003 | Liljedahl et al. ............ 435/69.1 |
| 2004/0019002 A1* | 1/2004 | Choulika et al. ................ 514/44 |
| 2005/0026157 A1 | 2/2005 | Baltimore et al. | |
| 2005/0064474 A1 | 3/2005 | Urnov et al. | |
| 2005/0208489 A1* | 9/2005 | Carroll et al. ..................... 435/6 |
| 2006/0063231 A1 | 3/2006 | Li et al. | |
| 2006/0188987 A1 | 8/2006 | Guschan et al. | |
| 2007/0134796 A1 | 6/2007 | Holmes et al. | |
| 2008/0015164 A1 | 1/2008 | Collingwood | |
| 2008/0131962 A1 | 6/2008 | Miller | |
| 2008/0159996 A1 | 7/2008 | Ando et al. | |
| 2009/0111119 A1 | 4/2009 | Doyon et al. | |
| 2009/0205083 A1* | 8/2009 | Gupta et al. .................. 800/298 |

FOREIGN PATENT DOCUMENTS

| | | |
|---|---|---|
| EP | 1348335 A1 | 10/2003 |
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | 03080809 A2 | 10/2003 |
| WO | WO 2007/014275 A2 | 1/2007 |
| WO | WO 2008/133938 A2 | 4/2008 |
| WO | 2008151081 A1 | 12/2008 |

OTHER PUBLICATIONS

Chandrasegaran (Biol. Chem., 1999, vol. 380, p. 841-848).*
Bibikova (MCB, Jan. 2001, vol. 21, No. 1, p. 289-297).*
Porteus (Nature Biotech., 2005, vol. 23, No. 8, p. 967-973).*
Wu (Cell Mol. Lif Science, 2007, vol. 64, 2933-2944).*
Santiago (PNAS, Apr. 2008, vol. 105, No. 15, p. 5809-5814).*
Doyon (Nature Biotech., Jun. 2008, vol. 26, No. 6, p. 702-708).*
Perez (Nature Biotech., Jul. 2008, vol. 26, No. 6, p. 808-816).*

(Continued)

*Primary Examiner* — Michael Wilson
(74) *Attorney, Agent, or Firm* — Dahna S. Pasternak; Pasternak Patent Law

(57) ABSTRACT

Disclosed herein are methods and compositions for genome editing of one or more loci in a rat, using fusion proteins comprising a zinc-finger protein and a cleavage domain or cleavage half-domain. Polynucleotides encoding said fusion proteins are also provided, as are cells comprising said polynucleotides and fusion proteins.

2 Claims, 30 Drawing Sheets

(56) References Cited

OTHER PUBLICATIONS

Carroll (Gene Therapy, Sep. 11, 2008, vol. 15, p. 1463-1468).*
Beumer (PNAS, Dec. 16, 2008, vol. 105, No. 50, p. 19821-19826).*
Geurts (Science, Jul. 24, 2009, vol. 325, No. 5939, p. 433-435, and Supplemental Materials associated therewith).*
Remy (Transgenic Res. Published online Sep. 26, 2009, vol. 19, p. 363-371).*
Mashimo (PLoS ONE, Jan. 2010, vol. 5, No. 1, e8870, p. 1-7).*
Urnov (Nature Reviews Genetics, Sep. 2010, vol. 11, p. 636-646).*
Urnov (Nature 2005, vol. 435, No. 7042, p. 646-651).*
Urnov (Nature, 2005, vol. 435, No. 7042, p. 646-651).*
Hammerschmidt (Methods Cell Biol., 1999, vol. 59, p. 87-115).*
Ashworth, et al., "Computational Redesign of Endonuclease DNA Binding and Cleavage Specificity," *Nature* 441:656-659 (2006).
Beerli, et al., "Engineering Polydactyl Zinc-Finger Transcription Factors," *Nature Biotechnology* 20:135-141 (2002).
Bitinate, et al., "FOKI Dimerization Is Required for DNA Cleavage," *PNAS USA* 95:10570-10575 (1998).
Boch, et al., "Breaking the Code of DNA Binding Specificity of TAL-Type III Effectors," *Science* 326:1509-1512 (2009).
Chevalier, et al., "Design, Activity, and Structure of a Highly Specific Artificial Endonuclease," *Molecular Cell* 10:895-905 (2002).
Choo, et al., "Advances in Zinc Finger Engineering," *Curr. Opin. Struct. Biol.* 10:411-416 (2000).
Doyon, et al., "Heritable Targeted Gene Disruption in Zebrafish Using Designed Zinc-Finger Nucleases," *Nature Biotechnology* 26:702-708 (2008).
Epinat, et al., "A Novel Engineered Meganuclease Induces Homologous Recombination in Yeast and Mammalian Cells," *Nucleic Acids Research* 31:2952-2962 (2003).
Geurts, et al., "Knockout Rats via Embryo Microinjection of Zinc-Finger Nucleases," *Science* 325:433 (2009).
Goldberg, et al., "Distinct Factors Control Histone Variant H3.3 Localization at Specific Genomic Regions," *Cell* 140:678-691 with Supplemental information (2010).
Hockemeyer, et al., "Efficient Targeting of Expressed and Silent Genes in Human ESCS and IPSCS Using Zinc-Finger Nucleases," *Nature Biotechnology* 9:851-857 with Supplemental information (2009).

Isalan et al., "A Rapid, Generally Applicable Method to Engineer Zinc Fingers Illustrated by Targeting the HIV-1 Promoter," *Nat Biotechnol* 19:656-660 (2001).
Kim, et al., "Chimeric Restriction Endonuclease," *PNAS USA* 91:883-887 (1994).
Kim, et al., "Insertion and Deletion Mutants of FOKI Restriction Endonuclease," *J. Biol. Chem.* 269:31978-31982 (1994).
Li, et al., "Functional Domains in FOK I Restriction Endonuclease," *PNAS USA* 89:4275-4279 (1992).
Li, et al., "Alteration of the Cleavage Distance of FOK I Restriction Endonuclease by Insertion Mutagenesis," *PNAS USA* 90:2764-2768 (1993).
Lombardo, et al., "Gene Editing in Human Stem Cells Using Zinc Finger Nucleases and Integrase-Defective Lentiviral Vector Delivery," *Nature Biotechnology* 25:1298-1306 (2007).
Meng, et al., "Targeted Gene Inactivation in Zebrafish Using Engineered Zinc-Finger Nucleases," *Nat Biotech*, pp. 1-7 published online May 25, 2008 with Supplemental information (2008).
Michalkiewicz, et al., "Efficient Transgenic Rat Production by a Lentiviral Vector," *Am J Physiol Heart Circ Physiol* 293:H881-H894 (2007).
Moehle, et al., "Targeted Gene Addition Into a Specified Location in the Human Genome Using Designed Zinc Finger Nucleases," *PNAS USA* 104:3055-3060 (2007).
Moscou, et al., "A Simple Cipher Governs DNA Recognition by TAL Effectors," *Science* 326:1501 (2009).
Pabo, et al., "Design and Selection of Novel CYS2-HIS2 Zinc Finger Proteins," *Ann. Rev. Biochem.* 70:313-340 (2001).
Paques, et al., "Meganucleases and DNA Double-Strand Break-Induced Recombination: Perspectives for Gene Therapy," *Current Gene Therapy* 7:49-66 (2007).
Porteus, et al., "Mammalian Gene Targeting With Designed Zinc Finger Nucleases," *Molecular Therapy* 13:438-446 (2006).
Segal, et al., "Custom DNA-Binding Proteins Come of Age: Polydactyl Zinc-Finger Proteins," *Curr. Opin. Biotechnol.* 12:632-637 (2001).
Urnov, et al., "Highly Efficient Endogenous Human Gene Correction Using Designed Zinc-Finger Nucleases,," *Nature* 435:646-651 (2005).
Miller, et al., "An Improved Zinc-Finger Nuclease Architecture for Highly Specific Genome Editing," *Nature Biotechnol.* 25(7):778-785 (2007).

* cited by examiner

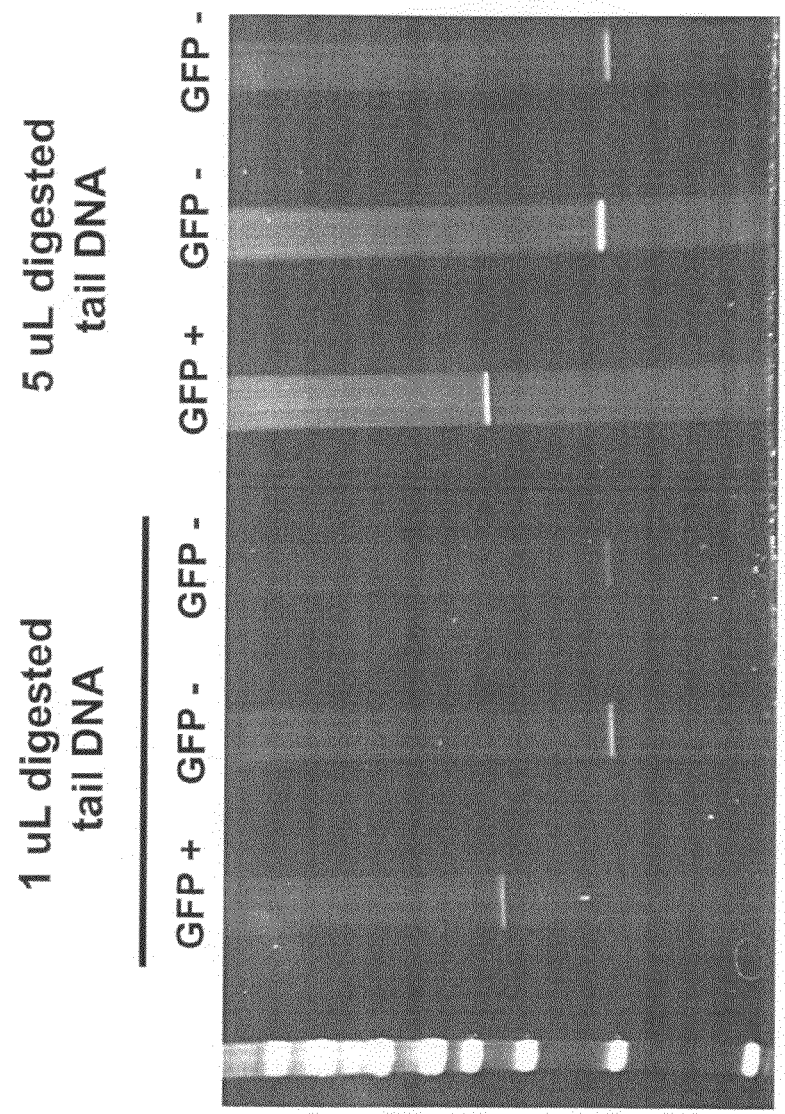
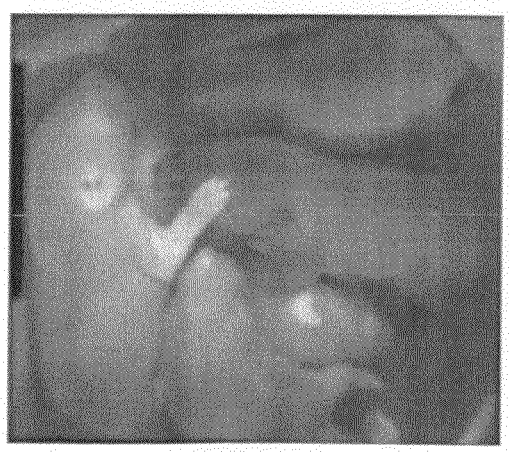
FIG. 4B
FIG. 4A

17747 / 17749

Exon 1

```
                           Rab38 ZFN-L                               Rab38 ZFN-R
ATCATCAAGCGCTACGTGCACCAAAACTTCTCCTCCCACTACGGGGCCACCATTGGTGTGGACTTCGCGCTGAAG    WT
ATCATCAAGCGCTACGTGCACCAAAACTTCTC:::::CTACCGGGCCACCATTGGTGTGGACTTCGCGCTGAAG    Δ6
ATCATCAAGCGCTAC:::::::::::::::::::::::::::::::::::::::::::GTGGACTTCGCGCTGAAG    Δ42
```

FIG. 10

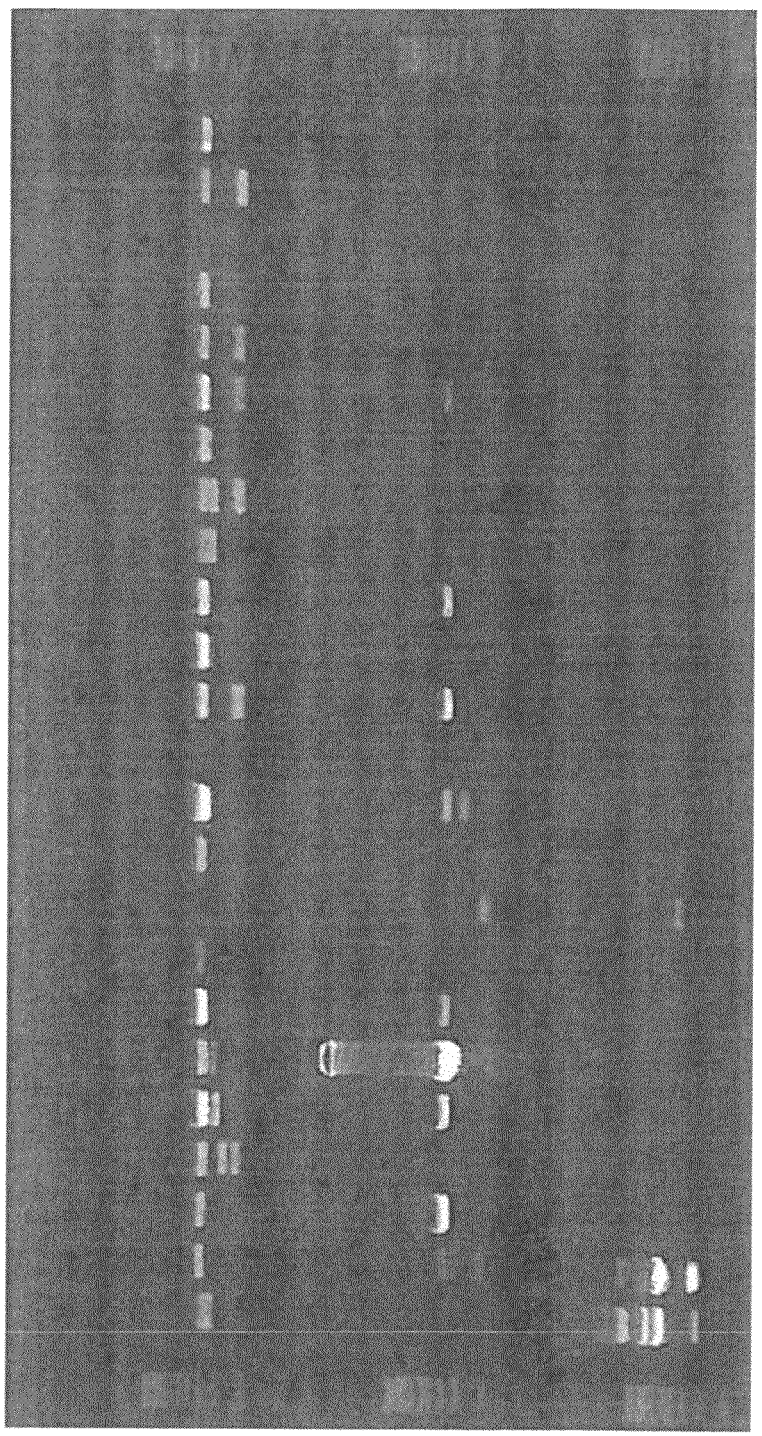

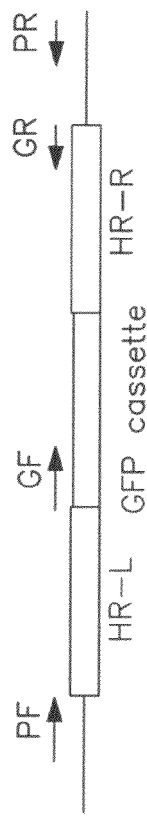
FIG. 23A
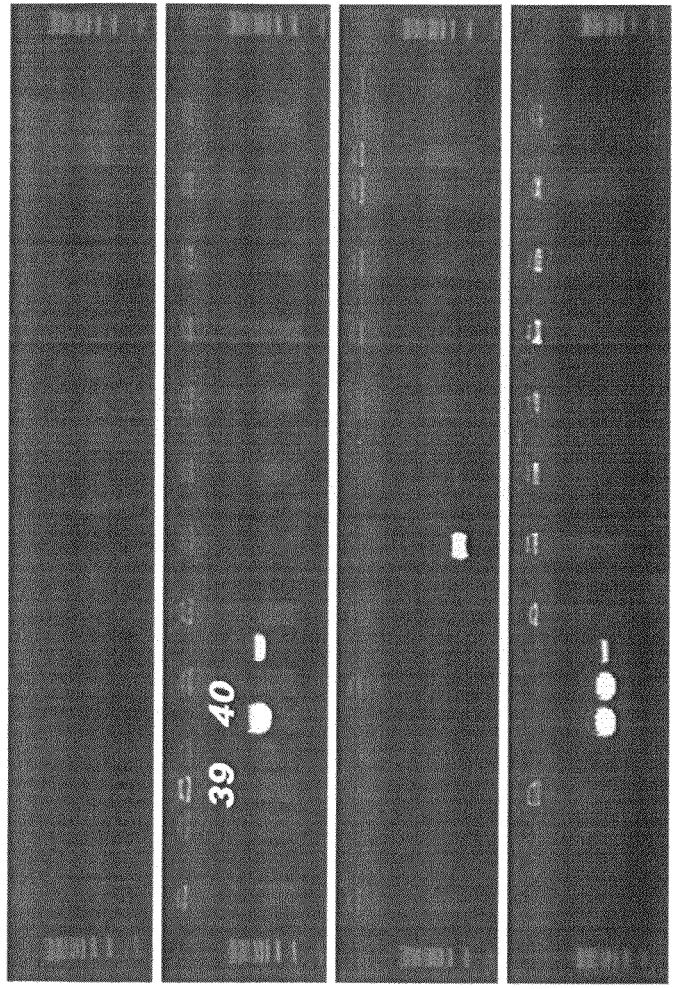
FIG. 23B
FIG. 23C
FIG. 23D
FIG. 23E

SEQUENCE LISTING

```
<160> NUMBER OF SEQ ID NOS: 184

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 1

Thr Gly Glu Lys Pro
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 2

Thr Gly Gly Gln Arg Pro
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 3

Thr Gly Gln Lys Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
      linker peptide

<400> SEQUENCE: 4

Thr Gly Ser Gln Lys Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat IgM and GFP

<400> SEQUENCE: 5

Arg Ser Ala His Leu Ser Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 6

Thr Ser Ala Asn Leu Ser Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 7

Arg Ser Asp Asn Leu Ser Val
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 8

Asp Arg Ser Asn Leu Thr Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: Chemically synthesized GFP zinc finger

<400> SEQUENCE: 9

Arg Ser Asp Thr Leu Ser Gln
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 10

Gln Arg Asp His Arg Ile Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 11

Asp Arg Ser Asn Leu Ser Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53 and GFP

<400> SEQUENCE: 12

Asp Arg Ser His Leu Ala Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 13

Arg Ser Asp His Leu Ser Ala
1               5

<210> SEQ ID NO 14
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 14

Asp Ser Ser Thr Arg Lys Thr
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 15

Thr Ser Gly Ser Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat IgM, GFP and p53

<400> SEQUENCE: 16

Arg Ser Asp Asp Leu Thr Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 17

Arg Ser Asp Asn Leu Ser Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 18

Asp Ser Ser Ser Arg Ile Lys
1               5

<210> SEQ ID NO 19
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 19

Arg Ser Ala Val Leu Ser Glu
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 20

Thr Asn Ser Asn Arg Ile Thr
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53, Rab38, IgM and GFP

<400> SEQUENCE: 21

Gln Ser Gly Asn Leu Ala Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 22

Gln Ser Gly Ser Leu Thr Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 23

Gln Ser Ser Asp Leu Arg Arg
1               5
```

-continued

```
<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 24

Arg Ser Asp Ala Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38, IgM and GFP

<400> SEQUENCE: 25

Thr Ser Gly Ser Leu Thr Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 26

Asp Ser Ser Ala Arg Lys Lys
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized GFP zinc finger

<400> SEQUENCE: 27

Arg Ser Asp Ser Leu Ser Val
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38, IgM and GFP

<400> SEQUENCE: 28

Asp Arg Ser Asp Leu Ser Arg
```

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat IgM and GFP

<400> SEQUENCE: 29

Asp Arg Ala Asn Leu Ser Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat IgM and GFP

<400> SEQUENCE: 30

Arg Ser Ala Asn Leu Ser Val
1               5

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of GFP zinc
      finger

<400> SEQUENCE: 31
gaccaggatg gg                                                       12

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of GFP zinc
      finger

<400> SEQUENCE: 32
gacggcgacg taaacg                                                   16

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of GFP zinc
      finger

<400> SEQUENCE: 33
gatgcggttc accagg                                                                                          16

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of GFP zinc
      finger

<400> SEQUENCE: 34
gaagggcatc gacttcaag                                                                                       19

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of GFP zinc
      finger

<400> SEQUENCE: 35
gttgtggctg ttgtagtt                                                                                        18

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of GFP zinc
      finger

<400> SEQUENCE: 36
atcatggccg acaag                                                                                           15

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 37

Thr Ser Ser Asn Arg Lys Thr
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Chemically synthesized zinc finger targeted to
      rat Rab38 and IgM gene

<400> SEQUENCE: 38

Arg Ser Asp Ser Leu Ser Ala
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 39

Arg Ser Asp Ala Leu Ala Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 40

Arg Ser Asp Ala Leu Thr Gln
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 41

Asp Arg Ser His Leu Thr Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 42

Gln Asn Ala His Arg Lys Thr
1               5

<210> SEQ ID NO 43
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53 and IgM

<400> SEQUENCE: 43

Arg Ser Asp Asn Leu Ser Glu
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat IgM and p53

<400> SEQUENCE: 44

Arg Ser Asp His Leu Ser Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 45

Thr Ser Ser Asp Leu Ser Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 46

Asn Lys Val Gly Leu Ile Glu
1               5

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of IgM zinc
      finger

<400> SEQUENCE: 47
```
aatttggtgg ccatgggc                                                    18

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of IgM zinc
      finger

<400> SEQUENCE: 48
agacaggggg ctctc                                                       15

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Synthetic oligonucleotide

<400> SEQUENCE: 49
gctaaccatg ttcatgcctt c                                                21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Synthetic oligonucleotide

<400> SEQUENCE: 50
catcctaggg ccgggattct c                                                21

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 51

Asp Arg Ser Ala Leu Ser Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat IgM and Rab38

<400> SEQUENCE: 52

Thr Ser Gly His Leu Ser Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 53

Arg Ser Asp Asn Leu Ser Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 54

His Asn Ala Thr Arg Ile Asn
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 55

Asp Asn Pro Asn Leu Asn Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 56

Arg Ser Ala Asn Leu Ala Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: Chemically synthesized zinc finger protein
      targeted to rat IgM

<400> SEQUENCE: 57

Arg Ser Asp Asn Leu Arg Glu
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 58

Thr Ser Gly Ser Leu Ser Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 59

Gln Ser Gly Ser Leu Thr Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 60

Arg Ser Asp Val Leu Ser Glu
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 61

Gln Ser Ser Asp Leu Ser Arg
1               5

<210> SEQ ID NO 62
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 62

Arg Ser Asp His Leu Ser Thr
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 63

His Ser Asn Ala Arg Lys Asn
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 64

Gln Ser Gly Asp Leu Thr Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 65

Arg Ser Asp Thr Leu Ser Val
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger protein
      targeted to rat IgM

<400> SEQUENCE: 66
```

```
Asp Asn Ser Thr Arg Ile Lys
1               5
```

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of IgM zinc
      finger

<400> SEQUENCE: 67
ctgaagtcat gcagggtgtc agaacctt                                         28

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of IgM zinc
      finger

<400> SEQUENCE: 68
ttgttctggt agttccagga gaaggaaa                                         28

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of IgM zinc
      finger

<400> SEQUENCE: 69
gtgctgtggg tgtggctagt gtttgtat                                         28

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of IgM zinc
      finger

<400> SEQUENCE: 70
aaggtgccat tggggtgact ttccatga                                         28

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of IgM zinc
      finger -continued

<400> SEQUENCE: 71
gagaggaccg tggacaagtc cactggta                                          28

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of IgM zinc
      finger

<400> SEQUENCE: 72
tcaccatgtg tggcagggcc tcgtggcc                                          28

<210> SEQ ID NO 73
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agtcagcttc ctgtctagaa gagaactggg tgtctatggg cc                          42

<210> SEQ ID NO 74
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
caaatgccac ctgtctgaat ggtttatgct ggcaatgggc t                           41

<210> SEQ ID NO 75
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggtgagaccc ctgtcttaac aaaagatggg ggggttggga a                           41

<210> SEQ ID NO 76
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gatccaaggc caccaactgg agtttaagac aaagggctct gc                          42

<210> SEQ ID NO 77
<211> LENGTH: 41
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 77
tgtccatggc ctcctcctct ttgctagagc ggtggctctc a                              41

<210> SEQ ID NO 78
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ggattgcccc ctgtcagtca cagcatatgg tggccataga tg                             42

<210> SEQ ID NO 79
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ggagaagccc atgtgtactc tttagttggt ggctctggga g                              41

<210> SEQ ID NO 80
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gcccataggc caacaactct caggctagac aacgggctct ca                             42

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 81

Asp Arg Ser Asn Leu Ser Ser
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 82

Arg Ser His Ser Leu Leu Arg
1               5
```

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 83

Gln Ser Gly His Leu Ser Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 84

His Lys Trp Gln Arg Asn Lys
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 85

Asp Arg Ser Val Leu Arg Arg
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 86

Asp Ser Ser Thr Arg Lys Lys
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to rat Rab38 and p53

<400> SEQUENCE: 87

Arg Ser Asp His Leu Ser Glu
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 88

Asp Lys Ser Asn Arg Lys Lys
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 89

Arg Ser Asp Thr Leu Ser Glu
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 90

Gln Lys Arg Asn Arg Thr Lys
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 91

Arg Ser Asp His Leu Ser Lys
1               5

<210> SEQ ID NO 92
<211> LENGTH: 7
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 92

His Asn Asp Ser Arg Thr Asn
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 93

Arg Ser Asp Tyr Leu Pro Arg
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 94

Gln Ser Asn Asp Leu Asn Ser
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 95

Gln Arg Val Thr Arg Asp Ala
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 96

His Ser Asn Ala Arg Lys Thr

```
<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat Rab38 gene

<400> SEQUENCE: 97

Ala Ser Lys Thr Arg Thr Asn
1               5

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of rat Rab38
      zinc finger

<400> SEQUENCE: 98
gaggagaagt tttggtgcac gtagcgct                                         28

<210> SEQ ID NO 99
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized target site of rat Rab38
      zinc finger

<400> SEQUENCE: 99
actaccgggc caccattggt gtggactt                                         28

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 100

Arg Ser Asp Asp Leu Ser Arg
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53
```

```
<400> SEQUENCE: 101

Asn Ser Gln His Leu Thr Glu
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 102

Gln Ser Ser His Leu Ser Arg
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 103

Arg Ser Asp Asn Leu Ala Arg
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 104

Arg Ser Asp His Leu Thr Thr
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 105

Arg Ser Asp Asn Leu Ser Gln
1               5

<210> SEQ ID NO 106
<211> LENGTH: 7
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 106

Ala Ser Asn Asp Arg Lys Lys
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 107

Arg Ser Ala Ala Leu Ala Arg
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 108

Arg Asn Gln His Arg Ile Thr
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 109

Asp Ser Arg Ser Arg Ile Asn
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized zinc finger targeted to
      rat p53

<400> SEQUENCE: 110

Asp Arg Ser His Leu Ser Arg
1               5
```

<210> SEQ ID NO 111
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized zinc finger targeted to
      rat p53

<400> SEQUENCE: 111
aagcggaagg ggcgggccat agcccggg                                           28

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized zinc finger targeted to
      rat p53

<400> SEQUENCE: 112
caggacgtgc ggaatgcgtt aagggaat                                           28

<210> SEQ ID NO 113
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized zinc finger targeted to
      rat p53

<400> SEQUENCE: 113
cttcccagtg ggaggtgaca gaaccctg                                           28

<210> SEQ ID NO 114
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized zinc finger targeted to
      rat p53

<400> SEQUENCE: 114
accggcgggt gcgggcggac tgcactta                                           28

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized zinc finger targeted to
      rat p53

<400> SEQUENCE: 115

```
ccggcgggtg cgggcggact gcacttag                                          28
```

<210> SEQ ID NO 116
<211> LENGTH: 35
<212> TYPE: DNA
<213> ORGANISM: Artificial Sequence
<220> FEATURE:
<223> OTHER INFORMATION: Description of Artificial Sequence: Synthetic
      primer: PXR 200 bp F Kpnl

<400> SEQUENCE: 116

```
aaaaggtacc tctgtgtttt tccgttctag tccag                                  35
```

<210> SEQ ID NO 117
<211> LENGTH: 35
<212> TYPE: DNA
<213> ORGANISM: Artificial Sequence
<220> FEATURE:
<223> OTHER INFORMATION: Description of Artificial Sequence: Synthetic
      primer: PXR 200 bp R Sacll

<400> SEQUENCE: 117

```
aaaaccgcgg ctgaagtata cgtggctctc ttgga                                  35
```

<210> SEQ ID NO 118
<211> LENGTH: 34
<212> TYPE: DNA
<213> ORGANISM: Artificial Sequence
<220> FEATURE:
<223> OTHER INFORMATION: Description of Artificial Sequence: Synthetic
      primer: PXR target F Notl

<400> SEQUENCE: 118

```
gtgtagcggc cgcgacaagg ccaatggcta tcac                                   34
```

<210> SEQ ID NO 119
<211> LENGTH: 34
<212> TYPE: DNA
<213> ORGANISM: Artificial Sequence
<220> FEATURE:
<223> OTHER INFORMATION: Description of Artificial Sequence: Synthetic
      primer: PXR target F Pmel

<400> SEQUENCE: 119

```
gtgtagttta acgacaagg ccaatggcta tcac                                    34
```

<210> SEQ ID NO 120
<211> LENGTH: 36
<212> TYPE: DNA
<213> ORGANISM: Artificial Sequence
<220> FEATURE:
<223> OTHER INFORMATION: Description of Artificial Sequence: Synthetic
      primer: PXR target R Notl

<400> SEQUENCE: 120

```
ttgtcgcggc cgctacacgg cagatttgaa gacctc                                 36
```

<210> SEQ ID NO 121
<211> LENGTH: 36
<212> TYPE: DNA
<213> ORGANISM: Artificial Sequence
<220> FEATURE:
<223> OTHER INFORMATION: Description of Artificial Sequence: Synthetic
      primer: PXR target R Pmel

<400> SEQUENCE: 121

```
ttgtcgttta aactacacgg cagatttgaa gacctc                                 36
```

<210> SEQ ID NO 122
<211> LENGTH: 39
<212> TYPE: DNA
<213> ORGANISM: Artificial Sequence
<220> FEATURE:
<223> OTHER INFORMATION: Description of Artificial Sequence: Synthetic primer: PXR 800 bp F Kpnl

<400> SEQUENCE: 122
aaaaggtacc tcagactggt ccagatttta gamaagggg                        39

<210> SEQ ID NO 123
<211> LENGTH: 36
<212> TYPE: DNA
<213> ORGANISM: Artificial Sequence
<220> FEATURE:
<223> OTHER INFORMATION: Description of Artificial Sequence: Synthetic primer: PXR 800 bp R Sacll

<400> SEQUENCE: 123
aaaaccgcgg ataaatctac tggttcgcca agctag                           36

<210> SEQ ID NO 124
<211> LENGTH: 32
<212> TYPE: DNA
<213> ORGANISM: Artificial Sequence
<220> FEATURE:
<223> OTHER INFORMATION: Description of Artificial Sequence: Synthetic primer: PXR 2Kb F Kpnl

<400> SEQUENCE: 124
aaaaggtacc gaggtagtag gaaatgcact tc                               32

<210> SEQ ID NO 125
<211> LENGTH: 33
<212> TYPE: DNA
<213> ORGANISM: Artificial Sequence
<220> FEATURE:
<223> OTHER INFORMATION: Description of Artificial Sequence: Synthetic primer: PXR 2Kb R Sacll

<400> SEQUENCE: 125
aaaaccgcgg gaagagaatt attgctgaca gtc                              33

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic primer: PXR 50 bp F

<400> SEQUENCE: 126
gagcctatca acgtagatga gg                                          22

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic primer: PXR 50 bp R

<400> SEQUENCE: 127
cttacatcct tcacaggtca tgac                                        24

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
      primer: rRosa26 200 bp F Kpnl

<400> SEQUENCE: 128
aaaaggtacc gggagtggat gaaggagttg                                     30

<210> SEQ ID NO 129
<211> LENGTH: 28
<212> TYPE: DNA
<213> ORGANISM: Artificial Sequence
<220> FEATURE:
<223> OTHER INFORMATION: Description of Artificial Sequence: Synthetic
      primer: rRosa26 200 bp R Sacll

<400> SEQUENCE: 129
aaaaccgcgg cggatcacaa gcaataat                                       28

<210> SEQ ID NO 130
<211> LENGTH: 33
<212> TYPE: DNA
<213> ORGANISM: Artificial Sequence
<220> FEATURE:
<223> OTHER INFORMATION: Description of Artificial Sequence: Synthetic
      primer: rRose26 target F Notl

<400> SEQUENCE: 130
cttcgcggcc gcgatctgca actggagtct ttc                                 33

<210> SEQ ID NO 131
<211> LENGTH: 33
<212> TYPE: DNA
<213> ORGANISM: Artificial Sequence
<220> FEATURE:
<223> OTHER INFORMATION: Description of Artificial Sequence: Synthetic
      primer: rRosa26 target F Pmel

<400> SEQUENCE: 131
cttcgtttaa acgatctgca actggagtct ttc                                 33

<210> SEQ ID NO 132
<211> LENGTH: 32
<212> TYPE: DNA
<213> ORGANISM: Artificial Sequence
<220> FEATURE:
<223> OTHER INFORMATION: Description of Artificial Sequence: Synthetic
      primer: rRosa26 target F Notl

<400> SEQUENCE: 132
gatcgcggcc gcgaagaagg gggaagggaa tc                                  32

<210> SEQ ID NO 133
<211> LENGTH: 32
<212> TYPE: DNA
<213> ORGANISM: Artificial Sequence
<220> FEATURE:
<223> OTHER INFORMATION: Description of Artificial Sequence: Synthetic
      primer: rRosa26 target R Pmel

<400> SEQUENCE: 133
gatcgtttaa acgaagaagg gggaagggaa tc                                  32

<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: Synthetic
      primer: rRosa26 800 bp F Kpnl

<400> SEQUENCE: 134
aaaaggtacc gcgtgtgaaa acacaaatgg                                30

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
      primer: rRosa26 800 bp R Sacll

<400> SEQUENCE: 135
aaaaccgcgg aaggaaagag gcattcatgg                                30

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      primer: rRosa26 2Kb F Kpnl

<400> SEQUENCE: 136
aaaaggtacc attatggagg ggaggactgg                                30

<210> SEQ ID NO 137
<211> LENGTH: 29
<212> TYPE: DNA
<213> ORGANISM: Artificial Sequence
<220> FEATURE:
<223> OTHER INFORMATION: Description of Artificial Sequence: Synthetic
      primer: rRosa26 2Kb R Sacll

<400> SEQUENCE: 137
aaaaccgcgg acatgtggca aacaggaga                                 29

<210> SEQ ID NO 138
<211> LENGTH: 19
<212> TYPE: DNA
<213> ORGANISM: Artificial Sequence
<220> FEATURE:
<223> OTHER INFORMATION: Description of Artificial Sequence: Synthetic
      primer: rRosa26 50 bp F

<400> SEQUENCE: 138
tgtcttctga ggaccgccc                                            19

<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      primer: rRosa26 50 bp R

<400> SEQUENCE: 139
ctgcccagaa gactcccgc                                            19

<210> SEQ ID NO 140

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer: mMdr1a 200 bp F Kpnl

<400> SEQUENCE: 140
aaaaggracc aacaacacta ggctcaggag                                              30

<210> SEQ ID NO 141
<211> LENGTH: 31
<212> TYPE: DNA
<213> ORGANISM: Artificial Sequence
<220> FEATURE:
<223> OTHER INFORMATION: Description of Artificial Sequence: Synthetic
      primer: mMdr1a 200 bp R Sacll

<400> SEQUENCE: 141
aaaaccgcgg cacatggcta agcacagcat g                                            31

<210> SEQ ID NO 142
<211> LENGTH: 31
<212> TYPE: DNA
<213> ORGANISM: Artificial Sequence
<220> FEATURE:
<223> OTHER INFORMATION: Description of Artificial Sequence: Synthetic
      primer: mMdr1a target F Notl

<400> SEQUENCE: 142
cctgcggccg cggactgtca gctggtatt g                                             31

<210> SEQ ID NO 143
<211> LENGTH: 31
<212> TYPE: DNA
<213> ORGANISM: Artificial Sequence
<220> FEATURE:
<223> OTHER INFORMATION: Description of Artificial Sequence: Synthetic
      primer: mMdr1a target F Pmel

<400> SEQUENCE: 143
cctgtttaaa cggactgtca gctggtatt g                                             31

<210> SEQ ID NO 144
<211> LENGTH: 31
<212> TYPE: DNA
<213> ORGANISM: Artificial Sequence
<220> FEATURE:
<223> OTHER INFORMATION: Description of Artificial Sequence: Synthetic
      primer: mMdr1a target R Notl

<400> SEQUENCE: 144
gtccgcggcc gcagggctga tggccaaaat c                                            31

<210> SEQ ID NO 145
<211> LENGTH: 31
<212> TYPE: DNA
<213> ORGANISM: Artificial Sequence
<220> FEATURE:
<223> OTHER INFORMATION: Description of Artificial Sequence: Synthetic
      primer: mMdr1a target R Pmel

<400> SEQUENCE: 145
gtccgtttaa acagggctga tggccaaaat c                                            31

<210> SEQ ID NO 146
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      primer: mMdr1a 800 bp F Kpnl

<400> SEQUENCE: 146
aaaaggtacc atgctgtgaa gcagatacc                                    29

<210> SEQ ID NO 147
<211> LENGTH: 34
<212> TYPE: DNA
<213> ORGANISM: Artificial Sequence
<220> FEATURE:
<223> OTHER INFORMATION: Description of Artificial Sequence: Synthetic
      primer: mMdr1a 800 bp R Sacll

<400> SEQUENCE: 147
aaaaccgcgg ctgaaaactg aatgagacat ttgc                              34

<210> SEQ ID NO 148
<211> LENGTH: 33
<212> TYPE: DNA
<213> ORGANISM: Artificial Sequence
<220> FEATURE:
<223> OTHER INFORMATION: Description of Artificial Sequence: Synthetic
      primer: mMdr1a 2KB F Kpnl

<400> SEQUENCE: 148
aaaaggtacc gtaatgttcc aattgcatct tcc                               33

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
      primer: mMdr1a 2KB R Sacll

<400> SEQUENCE: 149
aaaaccgcgg ctctcagttc tctgctgttg                                   30

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer: mMdr1a 50 bp F

<400> SEQUENCE: 150
gatttacccg tggctggaag                                              20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      primer: mMdr1a 50 bp R

<400> SEQUENCE: 151
ctggactcat ggacttcacc                                              20

<210> SEQ ID NO 152
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      primer: rMdr1a 200 bp F Kpnl

<400> SEQUENCE: 152
aaaaggtacc tggctcagga gaaaaattgt g                                    31

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
      primer: rMdr1a 200 bp R Sacll

<400> SEQUENCE: 153
aaaaccgcgg cacggctaaa gacagcatga                                      30

<210> SEQ ID NO 154
<211> LENGTH: 32
<212> TYPE: DNA
<213> ORGANISM: Artificial Sequence
<220> FEATURE:
<223> OTHER INFORMATION: Description of Artificial Sequence: Synthetic
      primer: rMdr1a target F Notl

<400> SEQUENCE: 154
ccctgcggcc gcggactgtc agctggtatt tg                                   32

<210> SEQ ID NO 155
<211> LENGTH: 32
<212> TYPE: DNA
<213> ORGANISM: Artificial Sequence
<220> FEATURE:
<223> OTHER INFORMATION: Description of Artificial Sequence: Synthetic
      primer: rMdr1a target F Pmel

<400> SEQUENCE: 155
ccctgtttaa acggactgtc agctggtatt tg                                   32

<210> SEQ ID NO 156
<211> LENGTH: 31
<212> TYPE: DNA
<213> ORGANISM: Artificial Sequence
<220> FEATURE:
<223> OTHER INFORMATION: Description of Artificial Sequence: Synthetic
      primer: rMdr1a target R Notl

<400> SEQUENCE: 156
gtccgcggcc gcagggctga tggccaaaat c                                    31

<210> SEQ ID NO 157
<211> LENGTH: 31
<212> TYPE: DNA
<213> ORGANISM: Artificial Sequence
<220> FEATURE:
<223> OTHER INFORMATION: Description of Artificial Sequence: Synthetic
      primer: rMdr1a target R Pmel

<400> SEQUENCE: 157
gtccgtttaa acagggctga tggccaaaat c                                    31

<210> SEQ ID NO 158
<211> LENGTH: 30
<212> TYPE: DNA
<213> ORGANISM: Artificial Sequence
```

<220> FEATURE:
<223> OTHER INFORMATION: Description of Artificial Sequence: Synthetic
      primer: rMdr1a 800 bp F Kpnl

<400> SEQUENCE: 158
aaaaggtacc ggagataggc tggtttgacg                                     30

<210> SEQ ID NO 159
<211> LENGTH: 29
<212> TYPE: DNA
<213> ORGANISM: Artificial Sequence
<220> FEATURE:
<223> OTHER INFORMATION: Description of Artificial Sequence: Synthetic
      primer: rMdr1a 700 bp R Sacll

<400> SEQUENCE: 159
aaaaccgcgg atggtggtag ttcggatgg                                      29

<210> SEQ ID NO 160
<211> LENGTH: 32
<212> TYPE: DNA
<213> ORGANISM: Artificial Sequence
<220> FEATURE:
<223> OTHER INFORMATION: Description of Artificial Sequence: Synthetic
      primer: rMdr1a 2Kb F Kpnl

<400> SEQUENCE: 160
aaaaaggtac caggttgttc ttggagatgt gc                                  32

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic
      primer: rMdr1a 2Kb T Sacll

<400> SEQUENCE: 161
aaaaccgcgg tcctcttggc tggtgagttt                                     30

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer: rMdr1a 50 bp F

<400> SEQUENCE: 162
gatttactcg cggctggaag                                                20

<210> SEQ ID NO 163
<211> LENGTH: 19
<212> TYPE: DNA
<213> ORGANISM: Artificial Sequence
<220> FEATURE:
<223> OTHER INFORMATION: Description of Artificial Sequence: Synthetic
      primer: rMdr1a 50 bp R

<400> SEQUENCE: 163
ctggactcac gggcttcac                                                 19

<210> SEQ ID NO 164
<211> LENGTH: 30
<212> TYPE: DNA
<213> ORGANISM: Artificial Sequence
<220> FEATURE:

```
<223> OTHER INFORMATION: Description of Artificial Sequence: Synthetic
      primer: PGKGFP-F NotI

<400> SEQUENCE: 164
aaagcggccg cttggggttg cgccttttcc                                      30

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      primer: PGKGFP-R NotI

<400> SEQUENCE: 165
aaaagcggcc gccatagagc ccaccgcatc                                      30

<210> SEQ ID NO 166
<211> LENGTH: 111
<212> TYPE: DNA
<213> ORGANISM: Rattus norvegicus

<400> SEQUENCE: 166
cctgcgagag cccctgtct gatgagaatt tggtggccat gggctgcctg gcccgggact      60
tcctgcccag ctccatttcc ttctcctgga actaccagaa caacactgaa g             111

<210> SEQ ID NO 167
<211> LENGTH: 111
<212> TYPE: DNA
<213> ORGANISM: Rattus norvegicus

<400> SEQUENCE: 167
cctgcgagag cccctgtct gatgagaatt tggtggccat gggctgcctg gcccgggact      60
tcctgcccag ctccatttcc ttctcctgga actaccagaa caacactgaa g             111

<210> SEQ ID NO 168
<211> LENGTH: 47
<212> TYPE: DNA
<213> ORGANISM: Rattus norvegicus

<400> SEQUENCE: 168
cctgcgagag cccctgtct cctggaacta ccagaacaac actgaag                   47

<210> SEQ ID NO 169
<211> LENGTH: 75
<212> TYPE: DNA
<213> ORGANISM: Rattus norvegicus

<400> SEQUENCE: 169
atcatcaagc gctacgtgca ccaaaacttc tcctcccact accgggccac cattggtgtg     60
gacttcgcgc tgaag                                                     75

<210> SEQ ID NO 170
<211> LENGTH: 69
<212> TYPE: DNA
<213> ORGANISM: Rattus norvegicus

<400> SEQUENCE: 170
atcatcaagc gctacgtgca ccaaaacttc tcctaccggg ccaccattgg tgtggacttc     60
gcgctgaag                                                            69
```

-continued

```
<210> SEQ ID NO 171
<211> LENGTH: 33
<212> TYPE: DNA
<213> ORGANISM: Rattus norvegicus

<400> SEQUENCE: 171
atcatcaagc gctacgtgga cttcgcgctg aag                                    33

<210> SEQ ID NO 172
<211> LENGTH: 42
<212> TYPE: DNA
<213> ORGANISM: Rattus norvegicus

<400> SEQUENCE: 172
ctgcgagagc ccctgtgtctc ctggaactac cagaacaaca ct                         42

<210> SEQ ID NO 173
<211> LENGTH: 106
<212> TYPE: DNA
<213> ORGANISM: Rattus norvegicus

<400> SEQUENCE: 173
ctgcgagagc ccctgtctg atgagaatttt ggtggccatg ggctgcctgg cccgggactt       60
cctgcccagc tccatttcct tctcctggaa ctaccagaac aacact                     106

<210> SEQ ID NO 174
<211> LENGTH: 106
<212> TYPE: DNA
<213> ORGANISM: Rattus norvegicus

<400> SEQUENCE: 174
ctgcgagagc ccctgtctg atgagaatttt ggtggccatg ggctgcctgg cccgggactt       60
cctgcccagc tccatttcct tctcctggaa ctaccagaac aacact                     106

<210> SEQ ID NO 175
<211> LENGTH: 42
<212> TYPE: DNA
<213> ORGANISM: Rattus norvegicus

<400> SEQUENCE: 175
ctgcgagagc ccctgtgtctc ctggaactac cagaacaaca ct                         42

<210> SEQ ID NO 176
<211> LENGTH: 106
<212> TYPE: DNA
<213> ORGANISM: Rattus norvegicus

<400> SEQUENCE: 176
ctgcgagagc ccctgtctg atgagaatttt ggtggccatg ggctgcctgg cccgggactt       60
cctgcccagc tccatttcct tctcctggaa ctaccagaac aacact                     106

<210> SEQ ID NO 177
<211> LENGTH: 42
<212> TYPE: DNA
<213> ORGANISM: Rattus norvegicus

<400> SEQUENCE: 177
ctgcgagagc ccctgtgtctc ctggaactac cagaacaaca ct                         42

<210> SEQ ID NO 178
<211> LENGTH: 106
<212> TYPE: DNA
```

<213> ORGANISM: Rattus norvegicus

<400> SEQUENCE: 178
ctgcgagagc ccctgtctg atgagaattt ggtggccatg ggctgcctgg cccgggactt      60
cctgcccagc tccatttcct tctcctggaa ctaccagaac aacact                   106

<210> SEQ ID NO 179
<211> LENGTH: 42
<212> TYPE: DNA
<213> ORGANISM: Rattus norvegicus

<400> SEQUENCE: 179
ctgcgagagc cccctgtctc ctggaactac cagaacaaca ct                        42

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
ggaggcaaga agatggattc                                                 20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gaatcggcac atgcagatct                                                 20

<210> SEQ ID NO 182
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Asp Glu Asn Leu
1               5

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Asp Glu Asn Leu Ala
1               5

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic

```
        peptide

<400> SEQUENCE: 184

Ser Cys Glu Ser Pro Leu Ser Asp Glu Asn Leu Val Ala
1               5                   10
```

METHOD OF DELETING AN IGM GENE IN AN ISOLATED RAT CELL

CROSS-REFERENCE TO RELATED APPLICATIONS

The present application claims the benefit of U.S. Provisional Application Nos. 61/200,985, filed Dec. 4, 2008; 61/205,970, filed Jan. 26, 2009 and 61/263,904, filed Nov. 24, 2009, the disclosures of which are hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the fields of genome engineering of rats, including somatic and heritable gene disruptions, genomic alterations, generation of alleles carrying random mutations at specific positions of rat genes and induction of homology-directed repair.

BACKGROUND

Rats (*Rattus norvegicus*) are a widely used animal model in the fields of hypertension, cardiovascular physiology, diabetes, metabolic disorders, behavioral studies and toxicity testing. Michalkiewicz et al. (2007) *J. Amer. Phys. Society* 293: H881-H894. The availability of these model systems, advances in rat genomics and sequence of the rat, human and mouse genomes have greatly accelerated the use of inbred rat models for discovery of the genetic basis of complex diseases and provided animal models for therapeutic drug discovery.

However, the advances in the information about the rat genome have not been accompanied by parallel progress in genome modification technology. Unlike mice, rat embryonic stem cell clones for gene targeting are not readily produced. Pronuclear injection has also proven difficult and has a poor success rate in generating transgenic rats. Michalkiewicz et al. (2007) *J. Amer. Phys. Society* 293:H881-H894 report generation of transgenic rats using a lentiviral construct expressing an enhanced green fluorescent protein (eGFP) reporter gene, where the eGFP transgene was found to be present in 1-4 copies integrated at random sites within the genome.

There remains a need for methods of modifying rat genomes in a targeted fashion. Precisely targeted site-specific cleavage of genomic loci offers an efficient supplement and/or alternative to conventional homologous recombination. Creation of a double-strand break (DSB) increases the frequency of homologous recombination at the targeted locus more than 1000-fold. More simply, the imprecise repair of a site-specific DSB by non-homologous end joining (NHEJ) can also result in gene disruption. Creation of two such DSBs results in deletion of arbitrarily large regions. The modular DNA recognition preferences of zinc-fingers protein allows for the rational design of site-specific multi-finger DNA binding proteins. Fusion of the nuclease domain from the Type II restriction enzyme Fok I to site-specific zinc-finger proteins allows for the creation of site-specific nucleases. See, for example, United States Patent Publications 20030232410; 20050208489; 20050026157; 20050064474; 20060188987; 20060063231; 20070134796; 2008015164; 20080131962; 2008015996 and International Publication WOs 07/014,275 and 2008/133938, which all describe use of zinc-finger nucleases and which are incorporated by reference in their entireties for all purposes.

SUMMARY

Disclosed herein are compositions for genome editing in rat, including, but not limited to: cleaving of one or more genes in rat resulting in targeted alteration (insertion, deletion and/or substitution mutations) in one or more rat genes, including the incorporation of these targeted alterations into the germline; targeted introduction of non-endogenous nucleic acid sequences, the partial or complete inactivation of one or more genes in rat; methods of inducing homology-directed repair and/or generation of random mutations encoding novel allelic forms of rat genes.

In one aspect, described herein is a zinc-finger protein (ZFP) that binds to target site in a region of interest in a rat genome, wherein the ZFP comprises one or more engineered zinc-finger binding domains. In one embodiment, the ZFP is a zinc-finger nuclease (ZFN) that cleaves a target genomic region of interest in rat, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). The ZFN may specifically cleave one particular rat gene sequence. Alternatively, the ZFN may cleave two or more homologous rat gene sequences.

The ZFN may bind to and/or cleave a rat gene within the coding region of the gene or in a non-coding sequence within or adjacent to the gene, such as, for example, a leader sequence, trailer sequence or intron, or within a non-transcribed region, either upstream or downstream of the coding region. In certain embodiments, the ZFN binds to and/or cleaves a coding sequence or a regulatory sequence of the target rat gene.

In another aspect, described herein are compositions comprising one or more of the zinc-finger nucleases described herein. In certain embodiments, the composition comprises one or more zinc-finger nucleases in combination with a pharmaceutically acceptable excipient.

In another aspect, described herein is a polynucleotide encoding one or more ZFNs described herein. The polynucleotide may be, for example, mRNA.

In another aspect, described herein is a ZFN expression vector comprising a polynucleotide, encoding one or more ZFNs described herein, operably linked to a promoter.

In another aspect, described herein is a rat host cell comprising one or more ZFN expression vectors. The rat host cell may be stably transformed or transiently transfected or a combination thereof with one or more ZFP expression vectors. In one embodiment, the rat host cell is an embryonic stem cell. In other embodiments, the one or more ZFP expression vectors express one or more ZFNs in the rat host cell. In another embodiment, the rat host cell may further comprise an exogenous polynucleotide donor sequence. In any of the embodiments, described herein, the rat host cell can comprise an embryo cell, for example a one or more cell embryo.

In another aspect, described herein is a method for cleaving one or more genes in a rat cell; the method comprising: (a) introducing, into the rat cell, one or more polynucleotides encoding one or more ZFNs that bind to a target site in the one or more genes under conditions such that the ZFN(s) is (are) expressed and the one or more genes are cleaved.

In yet another aspect, described herein is a method for introducing an exogenous sequence into the genome of a rat cell, the method comprising the steps of: (a) introducing, into the rat cell, one or more polynucleotides encoding one or more ZFNs that bind to a target site in the one or more genes under conditions such that the ZFN(s) is (are) expressed and the one or more genes are cleaved; and (b) contacting the cell with an exogenous polynucleotide; such that cleavage of the gene(s) stimulates integration of the exogenous polynucleotide into the genome by homologous recombination. In certain embodiments, the exogenous polynucleotide is integrated physically into the genome. In other embodiments, the exogenous polynucleotide is integrated into the genome by copying of the exogenous sequence into the host cell genome via nucleic acid replication processes (e.g., homology-directed repair of the double strand break). In yet other embodiments, integration into the genome occurs through non-homology dependent targeted integration (e.g. "end-capture"). In certain embodiments, the one or more nucleases are fusions between the cleavage domain of a Type IIS restriction endonuclease and an engineered zinc-finger binding domain.

In another embodiment, described herein is a method for modifying one or more gene sequence(s) in the genome of a rat cell, the method comprising (a) providing a rat cell comprising one or more target gene sequences; and (b) expressing first and second zinc-finger nucleases (ZFNs) in the cell, wherein the first ZFN cleaves at a first cleavage site and the second ZFN cleaves at a second cleavage site, wherein the gene sequence is located between the first cleavage site and the second cleavage site, wherein cleavage of the first and second cleavage sites results in modification of the gene sequence by non-homologous end joining. In certain embodiments, non-homologous end joining results in a deletion between the first and second cleavage sites. The size of the deletion in the gene sequence is determined by the distance between the first and second cleavage sites. Accordingly, deletions of any size, in any genomic region of interest, can be obtained. Deletions of 25, 50, 100, 200, 300, 400, 500, 600, 700, 800, 900, 1,000 nucleotide pairs, or any integral value of nucleotide pairs within this range, can be obtained. In addition deletions of a sequence of any integral value of nucleotide pairs greater than 1,000 nucleotide pairs can be obtained using the methods and compositions disclosed herein. In other embodiments, non-homologous end joining results in an insertion between the first and second cleavage sites. Methods of modifying the genome of a rat as described herein can be used to create models of animal (e.g., human) disease, for example by inactivating (partially or fully) a gene or by creating random mutations at defined positions of genes that allow for the identification or selection of transgenic rats carrying novel allelic forms of those genes, by insertion of humanized rat genes (to study, by way of a non-limiting example, drug metabolism) or by insertion of a mutant alleles of interest to examine, for example, the phenotypic affect of such a mutant allele.

In yet another aspect, described herein is a method for germline disruption of one or more target genes in rat, the method comprising modifying one or more gene sequences in the genome of one or more cells of a rat embryo by any of the methods described herein and allowing the rat embryo to develop, wherein that the modified gene sequences are present in at least a portion of gametes of the sexually mature rat.

In another aspect, described herein is a method of creating one or more heritable mutant alleles in rat loci of interest, the method comprising modifying one or more loci in the genome of one or more cells of a rat embryo by any of the methods described herein; raising the rat embryo to sexual maturity; and allowing the sexually mature rat to produce offspring; wherein at least some of the offspring comprise the mutant alleles.

In any of the methods described herein, the polynucleotide encoding the zinc finger nuclease(s) can comprise DNA, RNA or combinations thereof. In certain embodiments, the polynucleotide comprises a plasmid. In other embodiments, the polynucleotide encoding the nuclease comprises mRNA.

In a still further aspect, provided herein is a method for site specific integration of a nucleic acid sequence into a chromosome. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a zinc finger nuclease that recognizes the chromosomal site of integration, and (b) culturing the embryo to allow expression of the zinc finger nuclease, wherein a double stranded break introduced into the site of integration by the zinc finger nuclease is repaired, via homologous recombination with the DNA vector, so as to integrate the nucleic acid sequence into the chromosome. Suitable embryos may be derived from several different vertebrate species, including mammalian, bird, reptile, amphibian, and fish species. Generally speaking, a suitable embryo is an embryo that may be collected, injected, and cultured to allow the expression of a zinc finger nuclease. In some embodiments, suitable embryos may include embryos from rodents, companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a Drosophila embryo or a mosquito embryo.

Also provided is an embryo comprising at least one DNA vector, wherein the DNA vector comprises an upstream sequence and a downstream sequence flanking the nucleic acid sequence to be integrated, and at least one RNA molecule encoding a zinc finger nuclease that recognizes the chromosomal site of integration. Organisms derived from any of the embryos as described herein are also provided.

BRIEF DESCRIPTION OF THE DRAWINGS

FIG. 4, panels A and B, show targeted disruption of GFP by ZFNs in rat pups born from pronuclear injection of GFP-targeted ZFNs into embryos obtained from transgenic GFP rats. FIG. 4A shows the 5 pups under ultra-violet light, revealing 3 GFP positive animals and 2 animals that do not express GFP (GFP-negative). FIG. 4B shows results of PCR analysis of tail biopsies of GFP+ and GFP-pups.

FIG. 10 (SEQ ID NOS: 169-171) depicts sequence analysis of ZFN mediated modification of Rab38. Shown in this Figure is an alignment of the wildtype allele with two deletion alleles (Δ6 and Δ42).

FIG. 11, panels A to C, depict analysis of the pups obtained from crossing ZFN-IgM modified rats and a wild-type rat.

FIG. 15, panels A and B, depict methods of detecting RFLP integration.

FIG. 21, panels A and B, are photographic images of fluorescently stained DNA fragments resolved on an agarose gel. The leftmost and rightmost lanes contain a DNA ladder.

FIG. 23, panels A to E, are schematic and photographic images of fluorescently stained DNA fragments resolved on an agarose gel. FIG. 23A is a schematic showing the location of the primers used. FIGS. 23B and 23C show results from primers PF and GR. FIGS. 23D and 23E show results from primers PR+GF. Expected fragment size is 2.4 kb. Two out of forty fetuses were positive for GFP.

DETAILED DESCRIPTION

Figure 1:
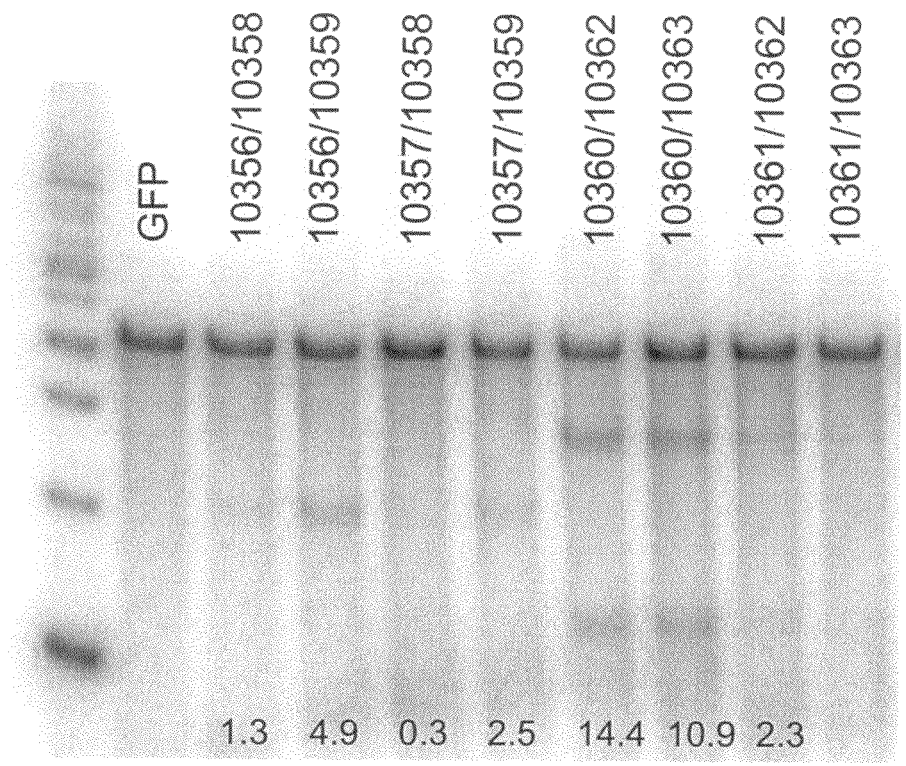
FIG. 1 shows Surveyor™ nuclease ("CEL-I") assays results of p53-specific ZFN pairs in rat C6 cells. The ZFN pair used in each lane is shown above the lane and the percent NHEJ activity as detected by the Surveyor mismatch assay is shown at the bottom.

Described herein are compositions and methods for genomic editing in rat (e.g., cleaving of genes; alteration of genes, for example by cleavage followed by insertion (physical insertion or insertion by replication via homology-directed repair) of an exogenous sequence and/or cleavage followed by non-homologous end joining (NHEJ); partial or complete inactivation of one or more genes; generation of alleles with random mutations to create altered expression of endogenous genes; etc.) and alterations of the rat genome which are carried into the germline. Also disclosed are methods of making and using these compositions (reagents), for example to edit (alter) one or more genes in a target rat cell. Thus, the methods and compositions described herein provide highly efficient methods for targeted gene alteration (e.g., knock-in) and/or knockout (partial or complete) of one or more rat genes and/or for randomized mutation of the sequence of any target allele, and, therefore, allow for the generation of animal models of human diseases.

The compositions and methods described herein provide rapid, complete, and permanent targeted disruption of endogenous loci in rats without the need for labor-intensive selection and/or screening and with minimal off-target effects. Whole animal gene knockouts can also be readily generated in a single-step by injecting ZFN mRNA or ZFN expression cassettes.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc-finger proteins have DNA-binding, RNA-binding and protein-binding activity.

A "zinc-finger DNA binding protein" (or binding domain) is a protein, or a domain within a larger protein, that binds DNA in a sequence-specific manner through one or more zinc-fingers, which are regions of amino acid sequence within the binding domain whose structure is stabilized through coordination of a zinc ion. The term zinc-finger DNA binding protein is often abbreviated as zinc-finger protein or ZFP.

Zinc-finger binding domains can be "engineered" to bind to a predetermined nucleotide sequence. Non-limiting examples of methods for engineering zinc-finger proteins are design and selection. A designed zinc-finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc-finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is, the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Prac-* tical Approach, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474; 2007/0218528 and 2008/0131962, incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule. An exogenous molecule can also be a molecule normally found in another species, for example, a human sequence introduced into a rat genome.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators; translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Zinc-Finger Nucleases

Described herein are zinc-finger nucleases (ZFNs) that can be used for genomic editing (e.g., cleavage, alteration, inactivation and/or random mutation) of one or more rat genes. ZFNs comprise a zinc-finger protein (ZFP) and a nuclease (cleavage) domain (e.g., cleavage half-domain).

A. Zinc-Finger Proteins

Zinc-finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc-finger binding domain can have a novel binding specificity, compared to a naturally-occurring zinc-finger protein. Engineering methods include, but are not limited to, rational design and various types of selection. Rational design includes, for example, using databases comprising triplet (or quadruplet) nucleotide sequences and individual zinc-finger amino acid sequences, in which each triplet or quadruplet nucleotide sequence is associated with one or more amino acid sequences of zinc-fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37.186; WO 98/53057; WO 00/27878; WO 01/88197 and GB 2,338,237. In addition, enhancement of binding specificity for zinc-finger binding domains has been described, for example, in co-owned WO 02/077227.

Selection of target sites; ZFPs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc-finger domains and/or multi-fingered zinc-finger proteins may be linked together using any suitable linker sequences, including for example, linkers of 5 or more amino acids in length (e.g., TGEKP (SEQ ID NO:1), TGQRP (SEQ ID NO:2), TGQKP (SEQ ID NO:3), and/or TGSQKP (SEQ ID NO:4)). See, also, U.S. Pat. Nos. 6,479,626; 6,903,185; and 7,153,949 for exemplary linker sequences 6 or more amino acids in length. The proteins described herein may include any combination of suitable linkers between the individual zinc-fingers of the protein.

As described below, in certain embodiments, a four-, five-, or six-finger binding domain is fused to a cleavage half-domain, such as, for example, the cleavage domain of a Type IIs restriction endonuclease such as FokI. One or more pairs of such zinc-finger/nuclease half-domain fusions are used for targeted cleavage, as disclosed, for example, in U.S. Patent Publication No. 20050064474.

For targeted cleavage, the near edges of the binding sites can separated by 5 or more nucleotide pairs, and each of the fusion proteins can bind to an opposite strand of the DNA target. All pairwise combinations 1 can be used for targeted cleavage of a rat gene. Following the present disclosure, ZFNs can be targeted to any sequence in the rat genome.

In some embodiments, the DNA binding domain is an engineered domain from a TAL effector derived from the plant pathogen Xanthomonas (see Boch et al, (2009) *Science* 29 Oct. 2009 (10.1126/science.117881) and Moscou and Bogdanove, (2009) *Science* 29 Oct. 2009 (10.1126/science.1178817).

B. Cleavage Domains

The ZFNs also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases,* Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc-finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc-finger-Fok I fusions, two fusion proteins, each comprising a FokI cleavage half-domain, can be used to reconstitute a catalytically active cleavage domain. Alternatively, a single polypeptide molecule containing a zinc-finger binding domain and two Fok I cleavage half-domains can also be used. Parameters for targeted cleavage and targeted sequence alteration using zinc-finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., Example 1 of U.S. Patent Publication No. 2008/0131962, the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in U.S. Patent Publication No. 20050064474 (Ser. No. 10/912,932, Example 5) and U.S. Patent Provisional Application Ser. No. 60/721,054 (Example 38).

C. Additional Methods for Targeted Cleavage in Rat

Any nuclease having a target site in any rat gene(s) can be used in the methods disclosed herein. For example, homing endonucleases and meganucleases have very long recognition sequences, some of which are likely to be present, on a statistical basis, once in a human-sized genome. Any such nuclease having a target site in a rat gene can be used instead of, or in addition to, a zinc-finger nuclease, for targeted cleavage in a rat gene.

Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66.

Delivery

The ZFNs described herein may be delivered to a target rat cell by any suitable means, including, for example, by injection of ZFN mRNA. See, Hammerschmidt et al. (1999) *Methods Cell Biol.* 59:87-115

Methods of delivering proteins comprising zinc-fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

ZFNs as described herein may also be delivered using vectors containing sequences encoding one or more of the ZFNs. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979, 539; 7,013,219; and 7,163,824, incorporated by reference herein in their entireties. Furthermore, it will be apparent that any of these vectors may comprise one or more ZFN encoding sequences. Thus, when one or more pairs of ZFNs are introduced into the cell, the ZFNs may be carried on the same vector or on different vectors. When multiple vectors are used, each vector may comprise a sequence encoding one or multiple ZFNs.

Conventional viral and non-viral based gene transfer methods can be used to introduce nucleic acids encoding engineered ZFPs in rat cells. Such methods can also be used to administer nucleic acids encoding ZFPs to rat cells in vitro. In certain embodiments, nucleic acids encoding ZFPs are administered for in vivo or ex vivo uses.

Non-viral vector delivery systems include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids. Viral vector delivery systems include DNA and RNA viruses, which have either episomal or integrated genomes after delivery to the cell. Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. No. 5,049,386, U.S. Pat. No. 4,946,787; and U.S. Pat. No. 4,897, 355) and lipofection reagents are sold commercially (e.g., Transfectam™ and Lipofectin™). Cationic and neutral lipids that are suitable for efficient receptor recognition lipofection of polynucleotides include those of Feigner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

As noted above, the disclosed methods and compositions can be used in any type of rat cell. Progeny, variants and derivatives of rat cells can also be used.

Applications

The disclosed methods and compositions can be used for genomic editing of any rat gene or genes. In certain applications, the methods and compositions can be used for inactivation of rat genomic sequences. In other applications, the methods and compositions allow for generation of random mutations, including generation of novel allelic forms of genes with different expression as compared to unedited genes or integration of humanized rat genes, which in turn allows for the generation of animal models. In other applications, the methods and compositions can be used for creating random mutations at defined positions of genes that allows for the identification or selection of animals carrying novel allelic forms of those genes. In other applications, the methods and compositions allow for targeted integration of an exogenous (donor) sequence into any selected area of the rat genome. Regulatory sequences (e.g. promoters) could be integrated in a targeted fashion at a site of interest. By "integration" is meant both physical insertion (e.g., into the genome of a host cell) and, in addition, integration by copying of the donor sequence into the host cell genome via the nucleic acid replication processes. Donor sequences can also comprise nucleic acids such as shRNAs, miRNAs etc. These small nucleic acid donors can be used to study their effects on genes of interest within the rat genome. Genomic editing (e.g., inactivation, integration and/or targeted or random mutation) of a rat gene can be achieved, for example, by a single cleavage event, by cleavage followed by non-homologous end joining, by cleavage followed by homology-directed repair mechanisms, by cleavage followed by physical integration of a donor sequence, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript. See, U.S.

Patent Publication Nos. 20030232410; 20050208489; 20050026157; 20050064474; 20060188987; 20060063231; and International Publication WO 07/014,275, the disclosures of which are incorporated by reference in their entireties for all purposes.

There are a variety of applications for ZFN-mediated genomic editing of rat. The methods and compositions described herein allow for the generation of rat models of human diseases. For example, editing of the p53 gene allows for the generation of a "cancer rat" that provides an animal model for studying cancer and testing cancer therapies.

EXAMPLES

Example 1

ZFNs Induce Targeted Disruption in Rat C6 Cells

ZFNs targeted to rat p53 were designed and incorporated into plasmids essentially as described in Urnov et al. (2005) *Nature* 435(7042):646-651. The recognition helices for representative rat p53 designs are shown below in Table 1. The target sites for these ZFNs are shown in Table 2.

TABLE 1 rat p53-specific ZFN designs

| ZFN Name | F1 | F2 | F3 | F4 |
|---|---|---|---|---|
| 10356 | RSDDLTR (SEQ ID NO: 16) | RSDHLSR (SEQ ID NO: 44) | DNPNLNR (SEQ ID NO: 55) | RSDDLSR (SEQ ID NO: 100) |
| 10358 | DNPNLNR (SEQ ID NO: 55) | RSDDLSR (SEQ ID NO: 100) | NSQHLTE (SEQ ID NO: 101) | QSSHLSR (SEQ ID NO102) |
| 10359 | QSGNLAR (SEQ ID NO: 21) | RSDDLTR (SEQ ID NO: 16) | NSQHLTE (SEQ ID NO: 101) | QSSHLSR (SEQ ID NO: 102) |
| 10357 | RSDDLTR (SEQ ID NO: 16) | RSDHLSR (SEQ ID NO: 44) | QSGNLAR (SE ID NO: 21) | RSDDLTR (SEQ ID NO: 16) |
| 10360 | RSDNLAR (SEQ ID NO: 103) | RSDHLTT (SEQ ID NO: 104) | RSDNLSQ (SEQ ID NO: 105) | ASNDRKK (SEQ ID NO: 106) |
| 10362 | RSDHLSE (SEQ ID NO: 87) | RSAALAR (SEQ ID NO: 107) | RSDHLSE (SEQ ID NO: 87) | RNQHRIT (SEQ ID NO: 108) |
| 10361 | RSDNLAR (SEQ ID NO: 103) | RSDHLTT (SEQ ID NO: 104) | RSDNLSE (SEQ ID NO: 43) | DSRSRIN (SEQ ID NO: 109) |
| 10363 | DRSHLSR (SEQ ID NO: 110) | RSDDLTR (SEQ ID NO: 16) | RSDHLSR (SEQ ID NO: 44) | DRSHLAR (SEQ ID NO: 12) |

TABLE 2 rat p53-specific ZFN targets

| ZFN Name | Target Site (5' to 3') |
|---|---|
| 10356 | aaGCGGAAGGGGCGggccatagcccggg (SEQ ID NO: 111) |

TABLE 2-continued rat p53-specific ZFN targets

| ZFN Name | Target Site (5' to 3') |
|---|---|
| 10358 | caGGACGTGCGGAAtgcgttaagggaat (SEQ ID NO: 112) |
| 10359 | caGGACGTGCGGAAtgcgttaagggaat (SEQ ID NO: 112) |
| 10357 | aaGCGGAAGGGGCGggccatagcccggg (SEQ ID NO: 111) |
| 10360 | ctTCCCAGTGGGAGgtgacagaaccctg (SEQ ID NO: 113) |
| 10362 | acCGGCGGGTGCGGgcggactgcactta (SEQ ID NO: 114) |
| 10361 | ctTCCCAGTGGGAGgtgacagaaccctg (SEQ ID NO: 113) |
| 10363 | ccGGCGGGtGCGGGCggactgcacttag (SEQ ID NO: 115) |

ZFN-encoding plasmids were transfected into rat C6 cells. To determine the ZFN activity at the p53 locus, CEL-I mismatch assays were performed essentially as per the manufacturer's instructions (Trangenomic SURVEYOR™). Cells were harvested and chromosomal DNA prepared using a Quickextract™ Kit according to manufacturer's directions (Epicentre®). The appropriate region of the p53 locus was PCR amplified using Accuprime™ High-fidelity DNA polymerase (Invitrogen). PCR reactions were heated to 94° C., and gradually cooled to room temperature. Approximately 200 ng of the annealed DNA was mixed with 0.33 µL CEL-I enzyme and incubated for 20 minutes at 42° C. Reaction products were analyzed by polyacrylamide gel electrophoresis in 1× Tris-borate-EDTA buffer.

Results are shown in FIG. 1 where various pairs of p53-specific ZFNs descried in Tables 1 and 2 were tested in combination. Percent mismatch, a measure of NHEJ activity are shown at the bottom of each lane. The results indicate that these ZFNs are active against this rat locus.

ZFNs targeted to GFP were designed and incorporated into plasmids essentially as described in Urnov et al. (2005) *Nature* 435(7042):646-651. ZFN pairs were screened for activity in a yeast-based chromosomal system as described in U.S. Ser. No. 12/284,887, entitled "Rapid in vivo Identification of Biologically Active Nucleases." Briefly, galactose-inducible ZFNs were transformed into a yeast strain containing an integrated Single Strand Annealing (ySSA) reporter, which consisted of the full eGFP sequence inserted between two overlapping segments of the MEL1 gene driven by the PGK promoter. The expression of the ZFNs was induced for 6 hours, then repressed for 18 hours, after which time a standard colorometric assay was used to quantify the amount of MEL1 protein in the supernatant.

The recognition helices for representative GFP zinc-finger designs are shown below in Table 3.

TABLE 3

GFP Zinc-finger Designs

| ZFN Name | F1 | F2 | F3 | F4 | F5 | F6 |
|---|---|---|---|---|---|---|
| 16833 "33" | RSAHLSR (SEQ ID NO: 5) | TSANLSR (SEQ ID NO: 6) | RSDNLSV (SEQ ID NO: 7) | DRSNLTR (SEQ ID NO: 8) | | |
| 16834 "34" | RSDTLSQ (SEQ ID NO: 9) | QRDHRIK (SEQ ID NO: 10) | DRSNLSR (SEQ ID NO: 11) | DRSHLAR (SEQ ID NO: 12) | DRSNLTR (SEQ ID NO: 8) | |
| 16855 "55" | RSDHLSA (SEQ ID NO: 13) | DSSTRKT (SEQ ID NO: 14) | TSGSLSR (SEQ ID NO: 15) | RSDDLTR (SEQ ID NO: 16) | TSANLSR (SEQ ID NO: 6) | |
| 16856 "56" | RSDNLST (SEQ ID NO: 17) | DSSSRIK (SEQ ID NO: 18) | RSAVLSE (SEQ ID NO: 19) | TNSNRIT (SEQ ID NO: 20) | RSAHLSR (SEQ ID NO: 5) | QSGNLAR (SEQ ID NO: 21) |
| 16859 "59" | TSGSLSR (SEQ ID NO: 15) | QSGSLTR (SEQ ID NO: 22) | TSGSLSR (SEQ ID NO: 15) | QSSDLRR (SEQ ID NO: 23) | RSDALSR (SEQ ID NO: 24) | TSGSLTR (SEQ ID NO: 25) |
| 16860 "60" | RSANLSV (SEQ ID NO: 30) | DRANLSR (SEQ ID NO: 29) | DRSDLSR (SEQ ID NO: 28) | RSDSLSV (SEQ ID NO: 27) | DSSARKK (SEQ ID NO: 26) | |

Target sites of the GFP zinc-finger designs are shown below in Table 4. Nucleotides in the target site that are contacted by the ZFP recognition helices are indicated in uppercase letters; non-contacted nucleotides indicated in lowercase.

TABLE 4

Target Sites of GFP Zinc-fingers

| ZFN Name | Target Site (5' to 3') | |
|---|---|---|
| 16833 | GACCAGGATGGG | (SEQ ID NO: 31) |
| 16834 | GACGGCGACgTAAACG | (SEQ ID NO: 32) |
| 16855 | GATGCGGTTcACCAGG | (SEQ ID NO: 33) |
| 16856 | GAAGGGCATCGAcTTCAAG | (SEQ ID NO: 34) |
| 16859 | GTTGTGGCTGTTGTAGTT | (SEQ ID NO: 35) |
| 16860 | ATCATGGCCGACAAG | (SEQ ID NO: 36) |

Active GFP-targeted ZFN expression constructs were transfected into rat C6 cells containing a GFP expression construct.

Figure 2:
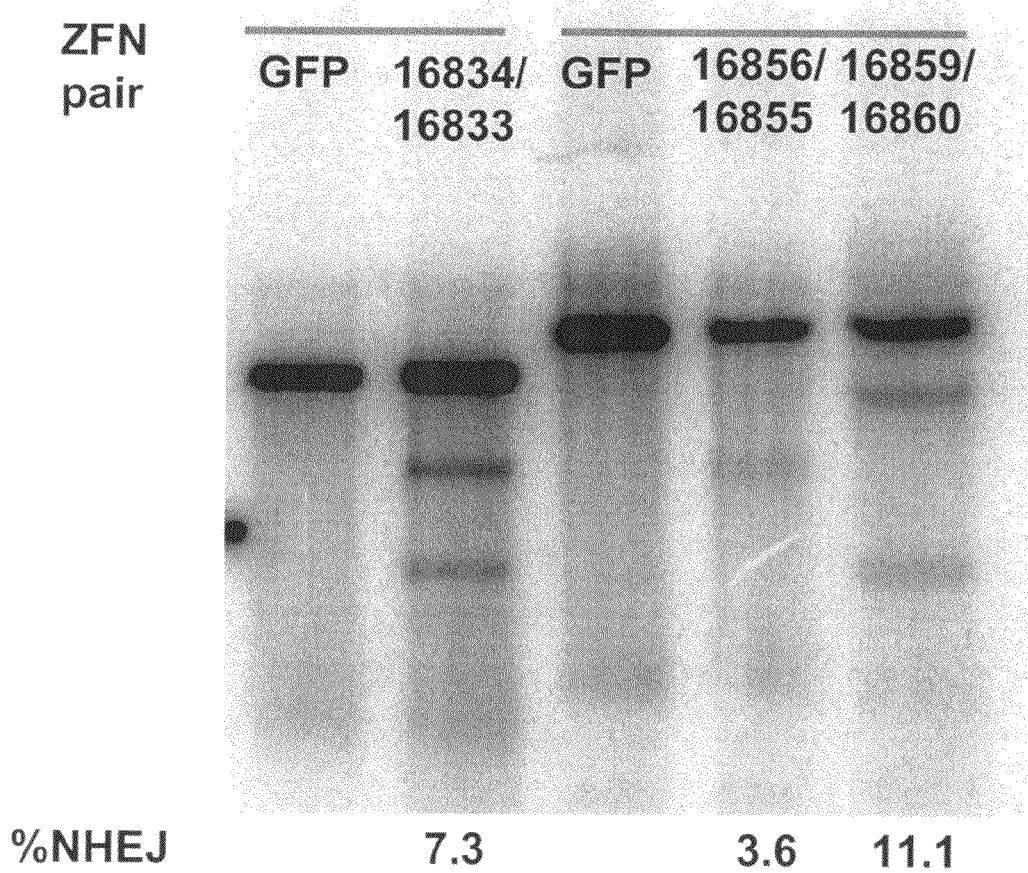
FIG. 2 shows Surveyor™ nuclease ("CEL-I") assays results of eGFP-targeted ZFN pairs 16834/16833, 16856/16855 and 16859/16860 in rat C6 cells carrying the eGFP gene. The ZFN pair used is shown above each lane and the % non-homologous end joining (% NHEJ) is indicated below each lane as appropriate.

As shown in FIG. 2, all ZFN pairs tested cleaved the GFP gene in the target cells.

Example 2

ZFNs Induce Targeted Disruption in Transgenic Rats

GFP-specific ZFNs as described in Example 1 were also introduced by pronuclear injection (PNI) or cytoplasmic injection (of ZFN mRNA) at varying concentrations into one-cell embryos obtained from transgenic rats expressing GFP described in Michalkiewicz et al. (2007) *J. Amer. Phys. Society* 293:H881-H894. See, FIG. 3.

The injected embryos were cultured for 2-3 days until they reached the 2-4 cell stage. Some of the 2-4 cell embryos were then transferred to pseudo-pregnant females. DNA was extracted from both cultured embryos and transferred embryos and cleavage of the GFP gene assessed.

Results of the different mode of injection and concentration of ZFNs injected into the embryos injected using ZFN pair 16859/16860 are shown in the Table 5 below.

TABLE 5

| Method of injection | ZFN conc. (ng/μL) | Embryos injected | Survived | Divided 2-cells | % | Transferred | Born |
|---|---|---|---|---|---|---|---|
| PNI | 1 | 40 | 23 | 19 | 83 | | |
| | 2 | 39 | 29 | 19 | 66 | | |
| | 1.5 | 36 | 25 | | | 25 | 5 |
| cytoplasmic | 5 | 40 | 26 | 16 | 62 | | |
| | 10 | 39 | 32 | 16 | 50 | | |
| | 20 | 38 | 31 | 24 | 77 | | |
| | 10 | 256 | 138 | | | 138 | |

GFP imaging of cytoplasmic injections of ZFN mRNA showed that many more ZFN-containing embryos failed to express GFP than uninjected embryos, indicating that no mosaicism was present in the cells in which ZFNs were active.

Figure 3:
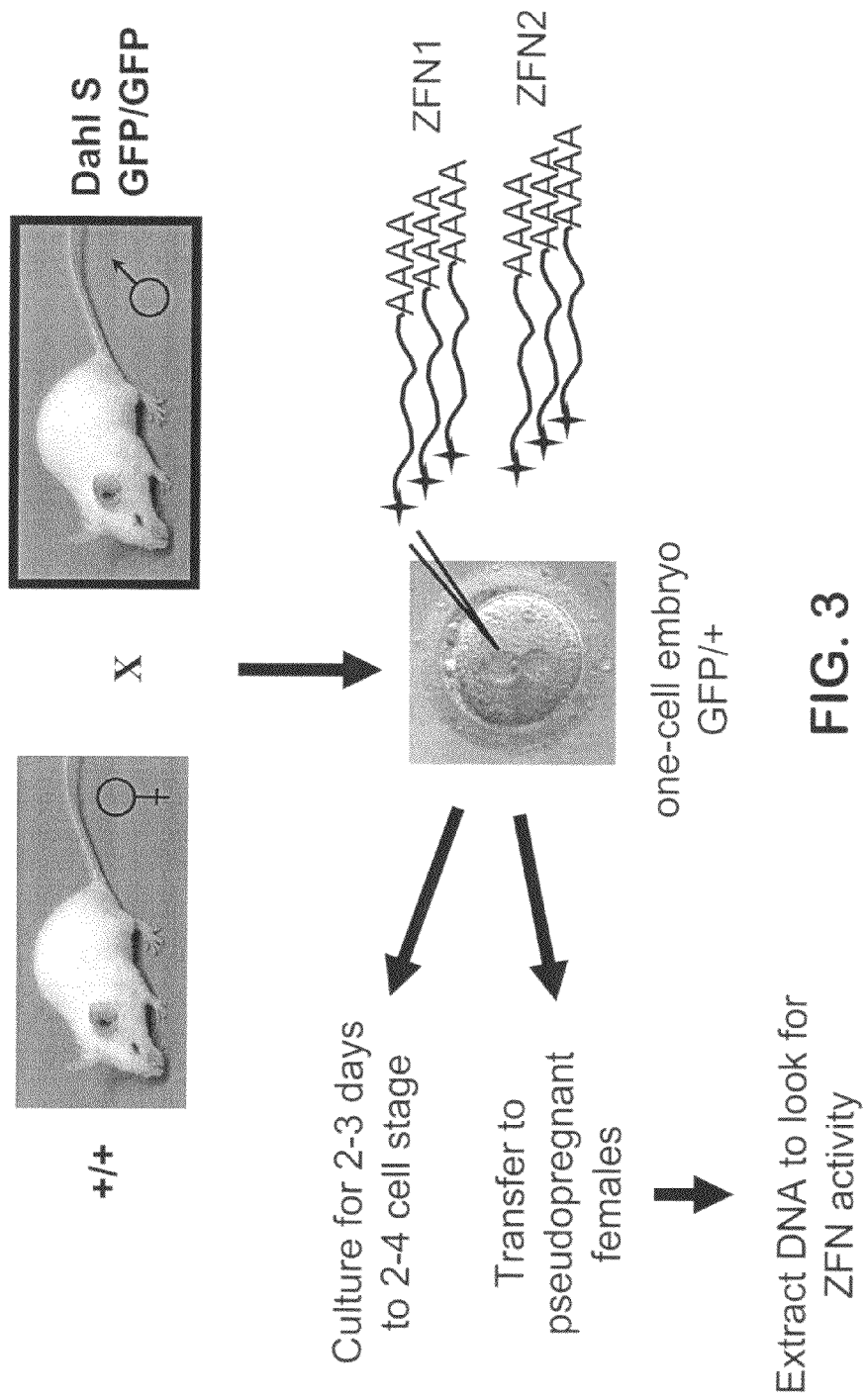
FIG. 3 is a schematic depicting targeted modification of a GFP transgene using ZFNs in transgenic GFP rats.
Figure 5:
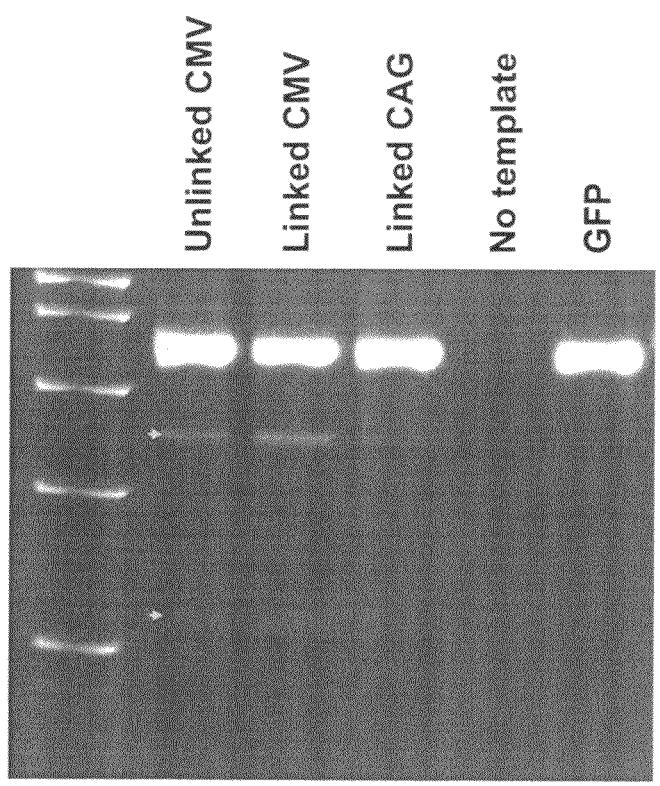
FIG. 5 depicts ZFN-mediated cleavage in exon 1 of endogenous IgM in C6 cells using ZFN pairs driven by the CMV promoter (CMV) or the CAG promoter. "Linked" refers to ZFN pairs on the same plasmid linked by the 2A peptide while "unlinked" refers to ZFN pairs not linked by the 2A peptide.
Figure 6:
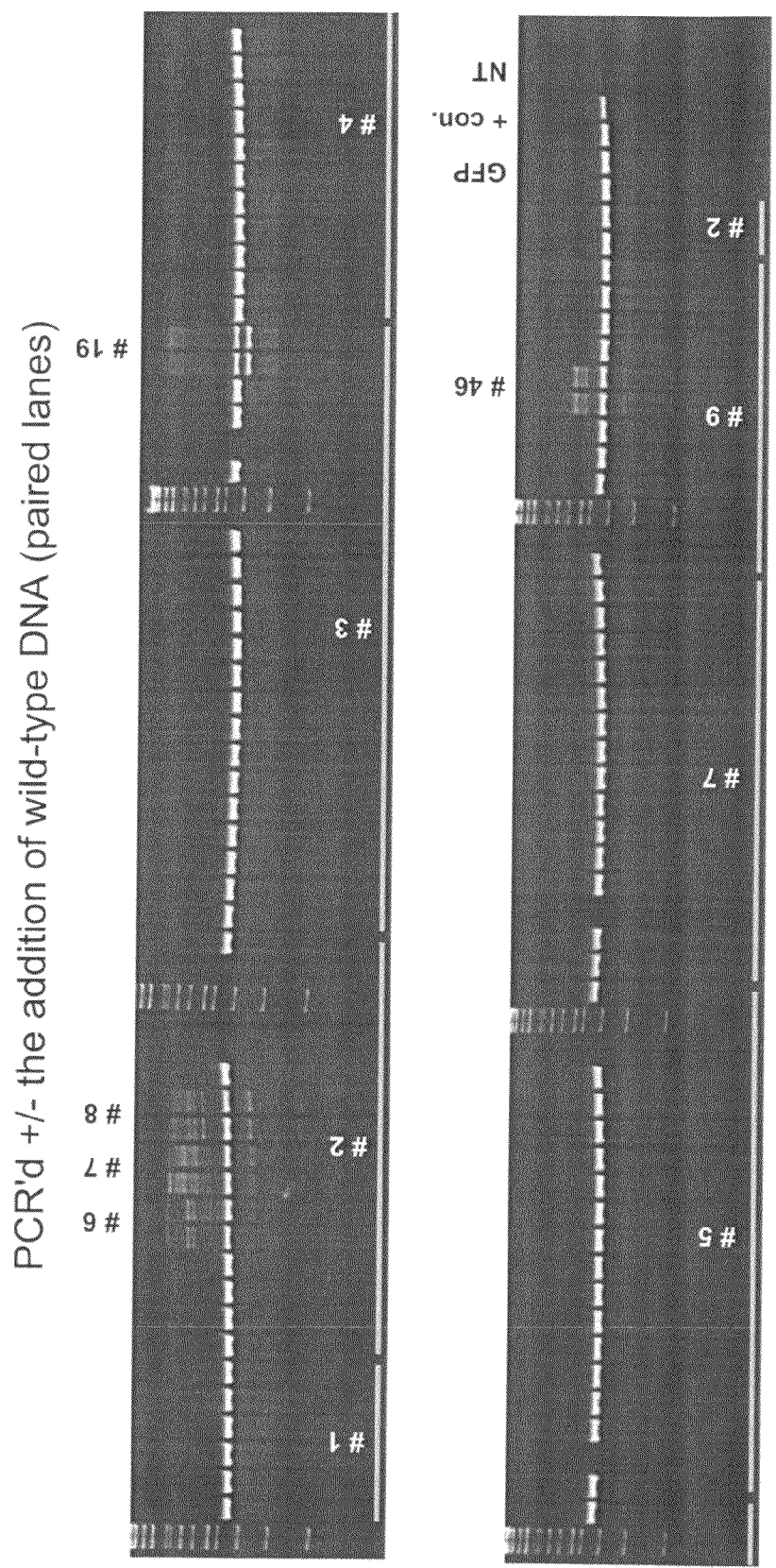
FIG. 6 depicts analysis, by Surveyor™ nuclease, of genomic DNA was prepared from the tails of 43 animals resulting from live births of IgM ZFN-injected one-cell embryos. As indicated, rats #6, 7, 8, 19, and 46 scored positive for modification at the IgM locus. Bars with white numbers indicate pups born from individual (numbered) mothers.

Five pups were born from pronuclear injection (PNI) of ZFNs into embryos that were transferred into pseudo-pregnant females. See, Table 5. As shown in FIG. 4A, 3 of the five pups expressed GFP while 2 pups did not.

Genomic DNA was prepared from the tails of the two GFP-negative animals and screened for modification via PCR. When compared to the wild-type eGFP locus, the regions bordering the site targeted by the ZFN 59/60 pair were significantly reduced, suggesting deletions of approximately 150 bp for both GFP-negative animals. Again, no mosaicism was evident in the tail biopsy as indicated by the absence of a wild-type eGFP band. These deletions were then directly analyzed by sequencing, which revealed deletions of 162 nt and 156 nt, resulting in the smaller bands evident in FIG. 4B. Furthermore, as shown in FIG. 4B, no mosaicism was evident in GFP negative pups since no wild-type eGFP band was detected.

Thus, ZFNs successfully modified the chromosomal GFP transgene.

Example 3

ZFNs Cleave Endogenous Rat Loci

ZFNs were designed to cleave endogenous loci as described below.

A. IgM

In one experiment, ZFNs were designed to cleave the endogenous rat IgM gene, as described above and were tested for cleavage activity in rat C6 cells. Exemplary rat IgM-targeted ZFPs are shown below in Table 6 below.

TABLE 6

IgM Zinc-finger Designs

| ZFN Name | F1 | F2 | F3 | F4 | F5 | F6 |
|---|---|---|---|---|---|---|
| 17747 | DRSHLTR (SEQ ID NO: 41) | RSDALTQ (SEQ ID NO: 40) | DRSDLSR (SEQ ID NO: 28) | RSDALAR (SEQ ID NO: 39) | RSDSLSA (SEQ ID NO: 38) | TSSNRKT (SEQ ID NO: 37) |
| 17749 | NKVGLIE (SEQ ID NO: 46) | TSSDLSR (SEQ ID NO: 45) | RSDHLSR (SEQ ID NO: 44) | RSDNLSE (SEQ ID NO: 43) | QNAHRKT (SEQ ID NO: 42) | |
| 17759 | DRSALSR (SEQ ID NO: 51) | TSGHLSR (SEQ ID NO: 52) | RSDNLST (SEQ ID NO: 53) | HNATRIN (SEQ ID NO: 54) | DRSALSR (SEQ ID NO: 51) | QSGNLAR (SEQ ID NO: 21) |
| 17756 | RSANLAR (SEQ ID NO: 56) | RSDNLRE (SEQ ID NO: 57) | TSGSLSR (SEQ ID NO: 58) | QSGSLTR (SEQ ID NO: 59) | RSDVLSE (SEQ ID NO: 60) | TSGSLTR (SEQ ID NO: 25) |
| 17767 | QSSDLSR (SEQ ID NO: 61) | RSDALAR (SEQ ID NO: 39) | TSGHLSR (SEQ ID NO: 52) | RSDALSR (SEQ ID NO: 39) | DRSDLSR (SEQ ID NO: 28) | |
| 17764 | RSDALAR (SEQ ID NO: 39) | RSDHLST (SEQ ID NO: 62) | HSNARKN (SEQ ID NO: 63) | DRSDLSR (SEQ ID NO: 28) | TSGHLSR (SEQ ID NO: 52) | |
| 17782 | RSANLSV (SEQ ID NO: 30) | DRANLSR (SEQ ID NO: 29) | RSDALAR (SEQ ID NO: 39) | DRSDLSR (SEQ ID NO: 28) | RSDDLTR (SEQ ID NO: 16) | |
| 17778 | RSAHLSR (SEQ ID NO: 5) | QSGDLTR (SEQ ID NO: 64) | RSDALAR (SEQ ID NO: 39) | RSDTLSV (SEQ ID NO: 65) | DNSTRIK (SEQ ID NO: 66) | |

Target sites of the rat IgM-targeted zinc-finger designs are shown below in Table 7. Nucleotides in the target site that are contacted by the ZFP recognition helices are indicated in uppercase letters; non-contacted nucleotides indicated in lowercase.

TABLE 7

Target Sites of IgM Zinc-fingers

| ZFN Name | Target Site (5' to 3') |
|---|---|
| 17747 | AATTTGGTGGCCATGGGC (SEQ ID NO: 47) |
| 17749 | AGACAGGGGGCTCTC (SEQ ID NO: 48) |
| 17759 | ctGAAGTCATGCAGGGTGTCagaaccTt (SEQ ID NO: 67) |
| 17756 | ttGTTCTGGTAGTTcCAGGAGaaggaaa (SEQ ID NO: 68) |
| 17767 | gtGCTGTGGGTGTGGCTagtgtttgtat (SEQ ID NO: 69) |
| 17764 | aaGGTGCCATTGGGGTGactttccatga (SEQ ID NO: 70) |
| 17782 | gaGAGGACcGTGGACAAGtccactggta (SEQ ID NO: 71) |
| 17778 | tcACCATGtGTGGCAGGGcctcgtggcc (SEQ ID NO: 72) |

All IgM-targeted ZFNs contained the EL/KK Fok I mutations as described in U.S. Patent Publication No. 2008/0131962. ZFN expression was driven by either the CAG or the CMV promoter. ZFN (1 µg each) were transfected into 200,000 C6 cells via Amaxa nucleofection using the solution SF and the Amaxa Shuttle 96-well nucleofector. The IgM locus was PCR amplified using GJC153F (5'-ggaggcaagaa-gatggattc-3') and GJC154R (5'-gaatcggcacatgcagatct-3') and ZFN cleavage was assayed with the Surveyor™ nuclease as described, for example, in U.S. Patent Publication Nos. 20080015164; 20080131962 and 20080159996.

In C6 cells, ZFN pair 17747/17749 cleaved 3% of chromosomes when the CMV promoter was used and approximately 1% when the CAG promoter was used (FIG. 4). This ZFN pair cleaved the rat IgM gene in the coding region of exon 1. Rat oocytes were injected with 10 ng/uL of a plasmid encoding ZFN pair 17747/17749 under the control of the CAG promoter using standard techniques. Oocytes were fertilized and implanted into pseudo-pregnant females. Out of 430 oocytes injected and implanted, 43 live births resulted. Genomic DNA was prepared from the tails of these 43 animals and screened for modification using the Surveyor™ nuclease.

Figure 7:
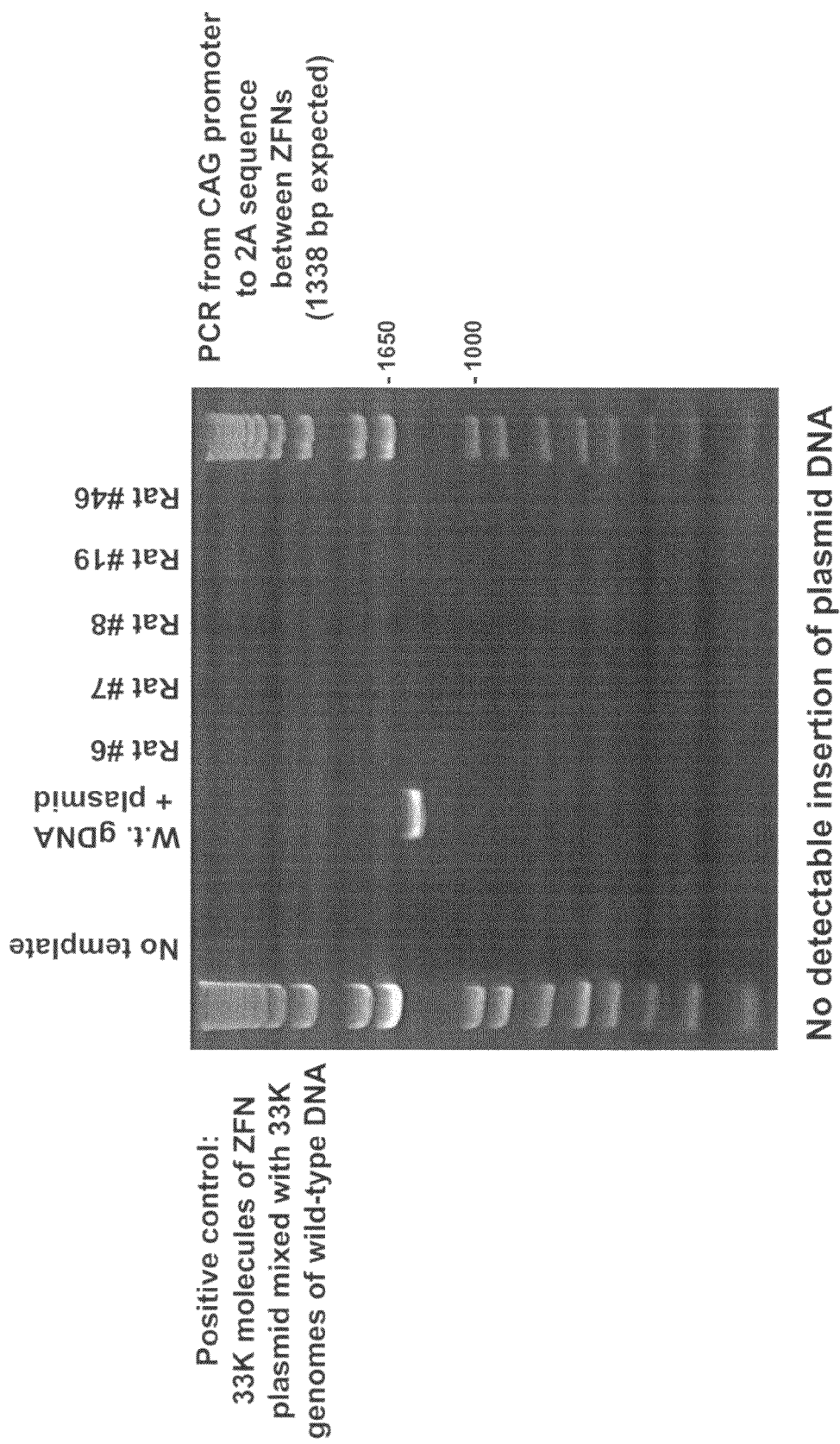
FIG. 7 depicts results of PCR analysis of the IgM modified rats (#6, 7, 8, 19, and 46 as identified in FIG. 6) for insertion of the ZFN plasmids into the genome.
Figure 8A:
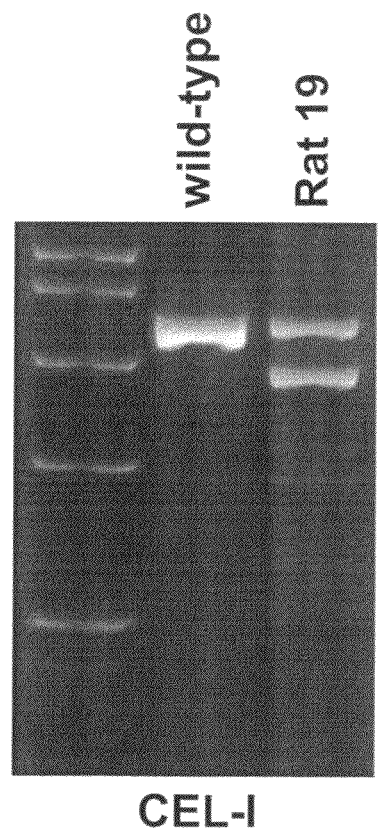
FIG. 8, panels and A and B, shows CEL-I and sequencing analysis of IgM modified rat #19. The alignment of the WT, Rat 19 wild type allele and the Rat 19 deletion allele sequences (Panel 8B) (SEQ ID NOS: 166-168) demonstrates the sequences that have been deleted from the Rat 19 deletion allele.
Figure 8B:
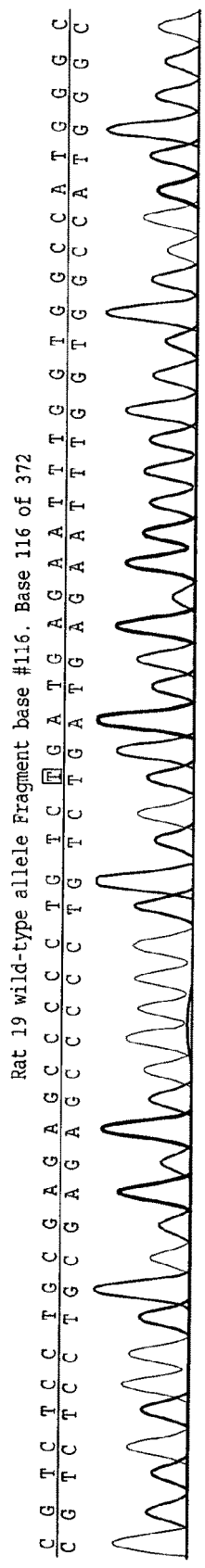
Figure 8B:
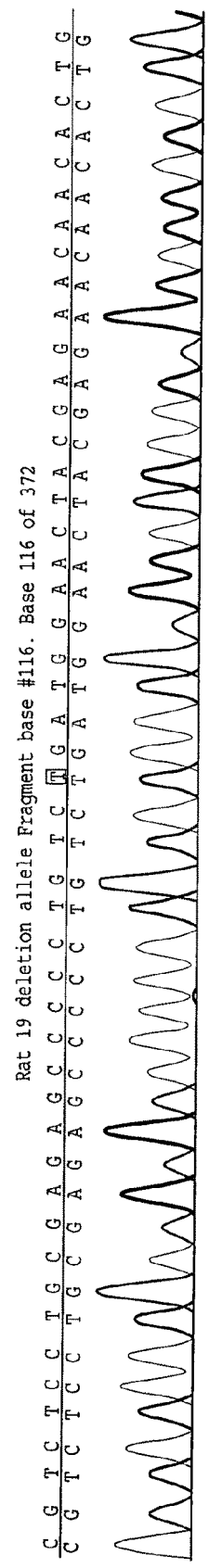

As shown in FIG. 7, five of the 43 animals (rats #6, 7, 8, 19, and 46) scored positive for modification at the IgM locus. The patterns of Surveyor™ nuclease digestion were identical both with and without the addition of wild-type rat genomic DNA, suggesting that none of the rats has a homozygous mutation.

GJC153F/GJC154R PCR products from the positive rats were cloned and sequenced. A description of the mutated alleles is in Table 8.

TABLE 8

| Rat Allele | Count | Approx. NHEJ % | Notes |
|---|---|---|---|
| 6 Wild-type | 8 | 49 | |
| 6 Δ9 | 2 | | in frame deletion of DEN |
| 7 Wild-type | 5 | 31 | |
| 7 Δ5 | 1 | | out of frame |
| 7 Δ13 | 1 | | out of frame |
| 7 Δ15 | 3 | | in frame deletion of SDENL (SEQ ID NO: 182) |
| 7 Δ18 | 1 | | in frame deletion of DENLA (SEQ ID NO: 183) |
| 7 Δ39 | 1 | | in frame del. of SCESPLSDENLVA (SEQ ID NO: 184) |
| 8 Wild-type | 7 | 25 | |
| 8 Δ3, 7b bp mut. | 3 | | in frame deletion of D, E->P |
| 8 Δ23 | 2 | | out of frame |

TABLE 8-continued

| Rat Allele | Count | Approx. NHEJ % | Notes |
|---|---|---|---|
| 19 Wild-type | 7 | 70 | |
| 19 Δ64 | 17 | | largest deletion, out of frame |
| 46 Wild-type | 9 | 47 | |
| 46 Δ5 | 2 | | out of frame |

Count refers to the number of time a particular sequence was isolated.
NHEJ, % is the approximate percentage of chromosomes modified in the tail DNA Sequencing of the IgM locus in these rats confirmed the results of the Surveyor™ nuclease assay. All deletions overlap the ZFN binding sites. The spectrum of small deletions seen here is typical of NHEJ-mediated mutation. Rats 7 and 8 have more than one mutated allele and are therefore mosaics for the IgM mutation. Although sequencing of rats 6, 19, and 46 gave only one mutated allele, they may be mosaic for IgM modification in other tissues.

Thus, ZFNs successfully modified the endogenous rat IgM locus.

To determine whether the ZFN plasmid itself integrated into the rat genome, a PCR-based assay was developed to test for ZFN plasmid integration. Briefly, rat genomic DNA and the ZFN plasmid were mixed so as to mimic a plasmid insertion frequency of once per genome. Performing 35 cycles of PCR amplification of this mixture with one oligo in the CAG promoter (5'-GCT AAC CAT GTT CAT GCC TTC-3') (SEQ ID NO:49) and another oligo in the 2A region of the plasmid (5'-CAT CCT AGG GCC GGG ATT CTC-3') (SEQ ID NO:50) gave a band of 1338 bp (FIG. 7, lane 3). When genomic DNA from wild-type and the five ZFN-modified rats was analyzed, no PCR product was detectable; indicating that insertion of the plasmid into the rat genome is not a high-frequency event.

In addition, IgM modified rat #19 was further analyzed by CEL-I assay and sequencing. As shown in FIGS. 7A and 7B, IgM-ZFNs produced a 64 base pair deletion in this rat in the IgM locus.

Figure 9A:
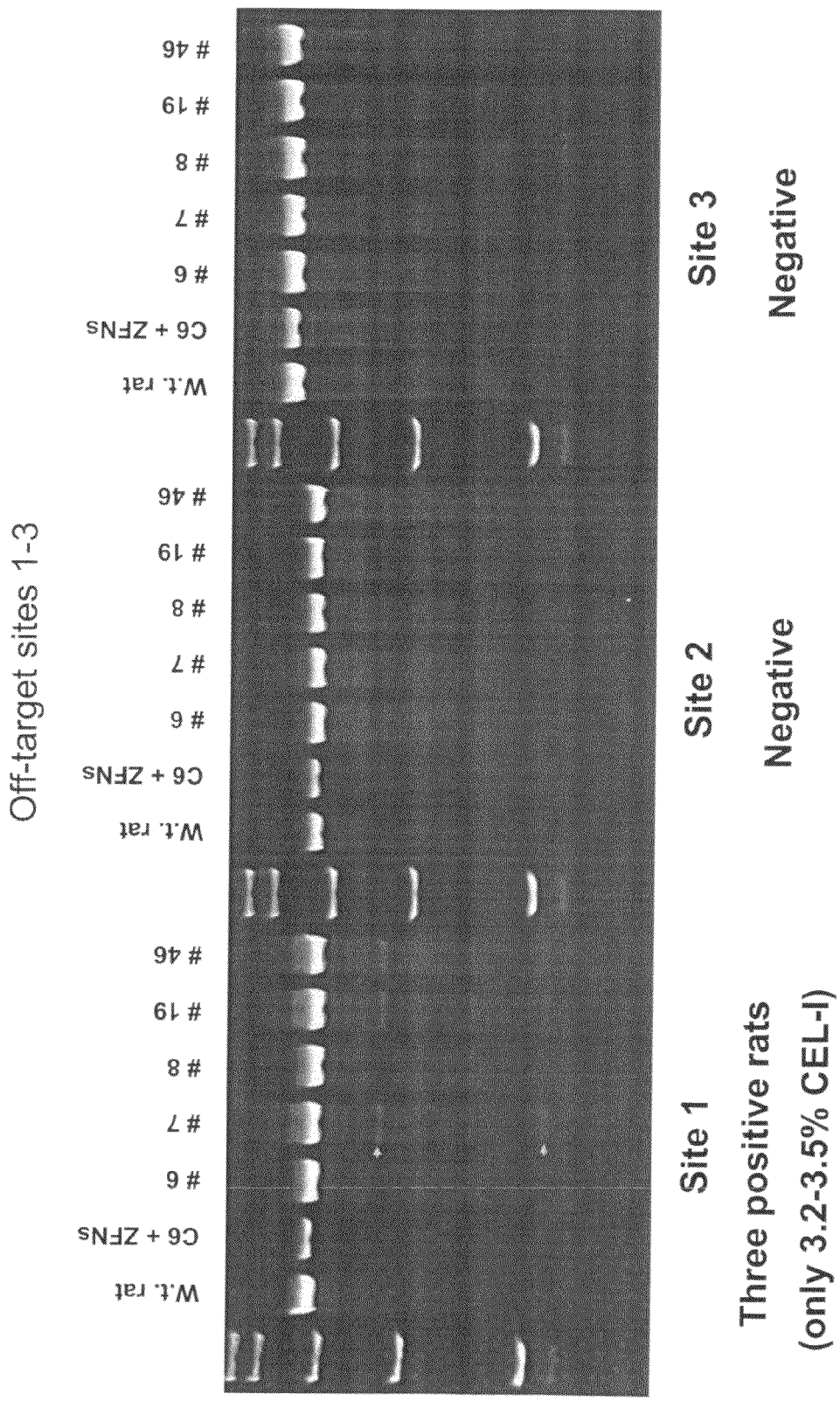
FIG. 9, panels A to C, depict analysis of IgM modified rats (#6, 7, 8, 19, and 46 as identified in FIG. 6) for activity at 8 different off-target sites. Off target sites (Site 1, Site 2 etc.) are as delineated in Table 9.
Figure 9B:
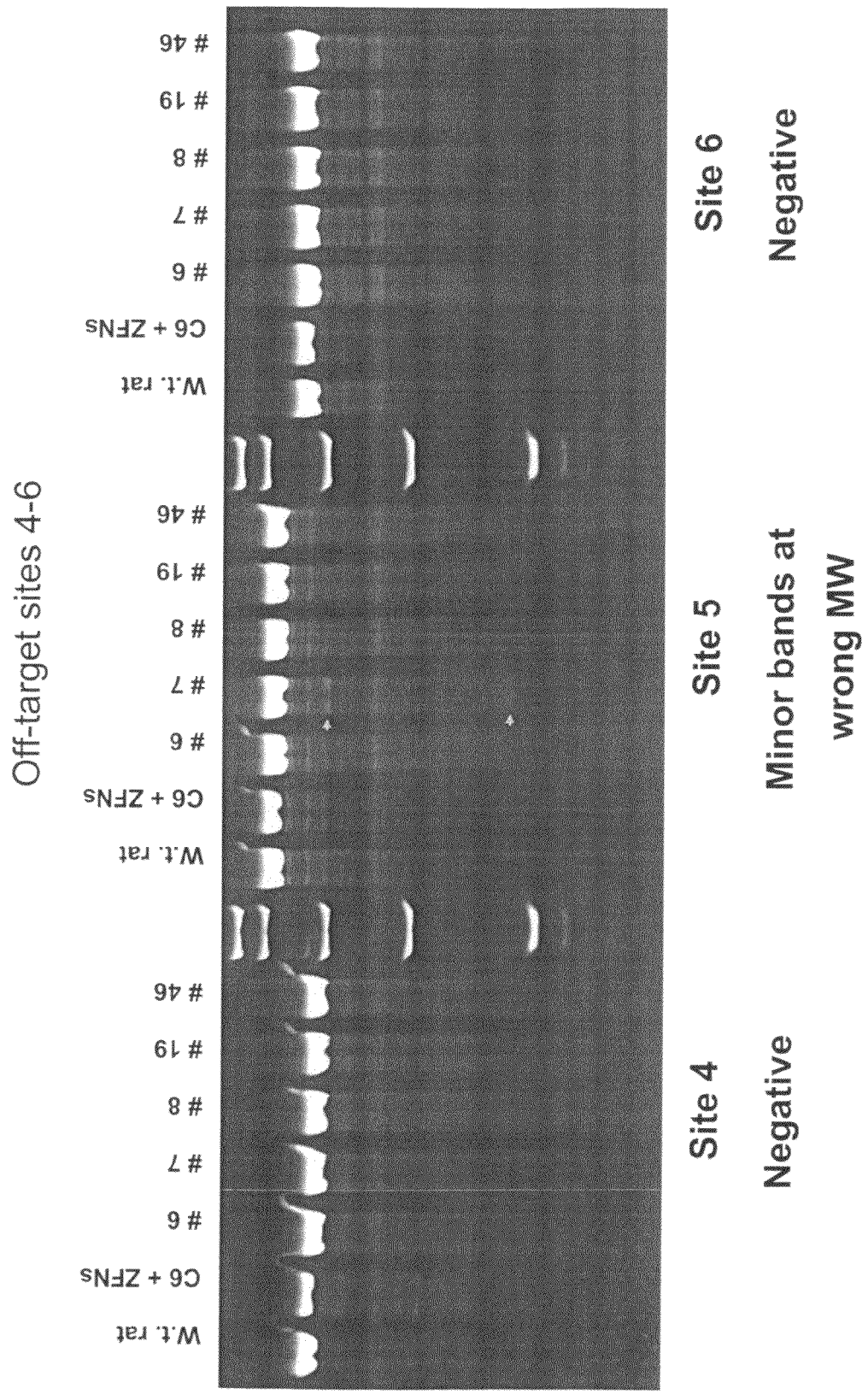
Figure 9C:
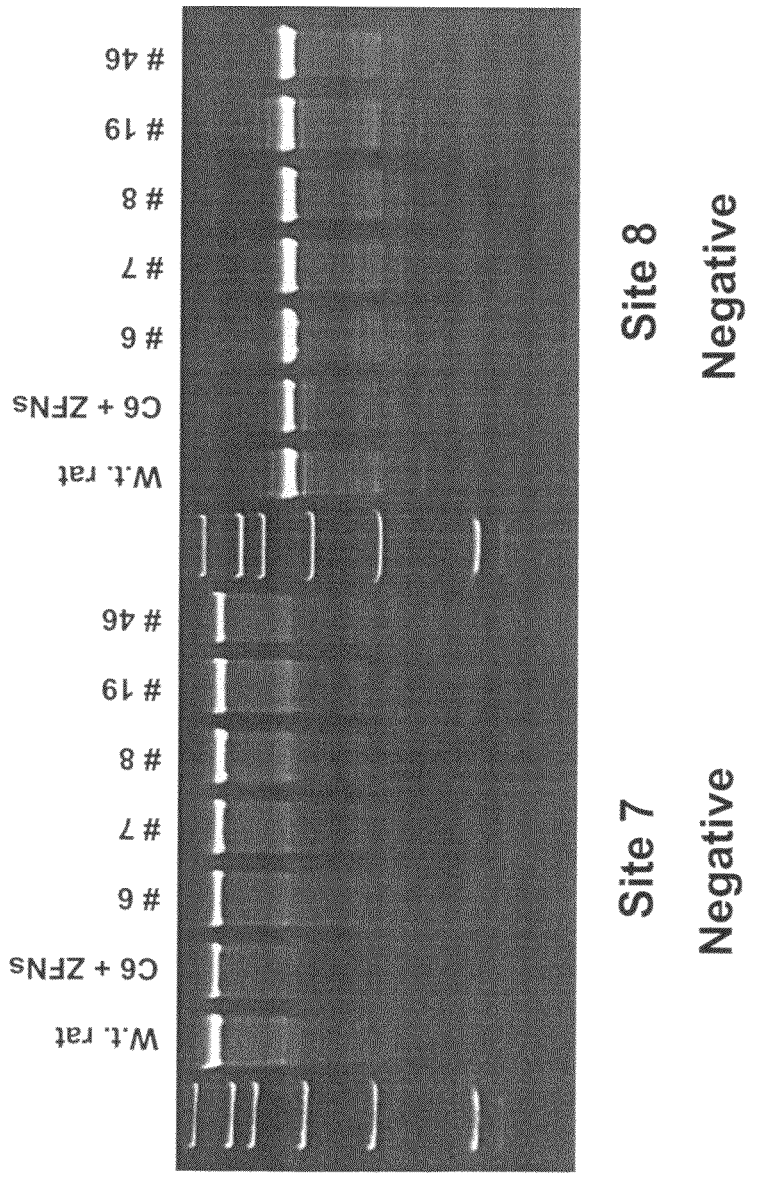

Finally, ZFNs cleavage at off-target sites was also evaluated. A computer algorithm was used to predict the location of the most likely off-target sites (Doyon et al (2008) Nature Biotechnology 26(6):702-708). All likely off-target sites were assayed for ZFN modification using the Surveyor™ nuclease assay as described above. The results of this analysis are shown in Table 9 and FIGS. 9A-C.

TABLE 9

| Site | Score | Sequence | Mm Gene | PCR Frag. | A Frag. | B Hit |
|---|---|---|---|---|---|---|
| 1 | 8.18E − 17 | AGtcAGCttCCTGTCTAGAAGA GAAcTgGGTGtCtATGGGCC (SEQ ID NO: 73) | 8 | 320 | 221 | 99 No |
| 2 | 2.90E − 18 | CaAatGCCaCCTGTCTGAATG GttTaTGcTGGCaATGGGCT (SEQ ID NO: 74) | 9 | 325 | 222 | 103 No |
| 3 | 1.67E − 18 | GGtGAGaCCCCTGTCTTAACA AAAgaTGGgGGggtTGGGaA (SEQ ID NO: 75) | 9 | 379 | 239 | 40 No |
| 4 | 7.75E − 19 | GatCCAaGGCCACCAAcTgGA GTTTAAGACAaaGGGCTCTgC (SEQ ID NO: 76) | 8 | 322 | 218 | 104 No |
| 5 | 6.44E − 19 | TGtCCATGGCCtCCtccTcTTT GCTAGAgcGGtGGCTCTCA (SEQ ID NO: 77) | 9 Pde4d | 396 | 200 | 196 No |

TABLE 9-continued

| Site | Score | Sequence | Mm | Gene | PCR | Frag. A | Frag. B | Hit |
|---|---|---|---|---|---|---|---|---|
| 6 | 1.49E − 19 | GGAttGCCCCCTGTCaGTCAC AGcATaTGGTGGCCATaGatG (SEQ ID NO: 78) | 8 | LOC499913 | 342 | 200 | 142 | No |
| 7 | 1.14E − 19 | GGAGAagCCCaTGTgTACTCT TtAgTTGGTGGCtcTGGGaG (SEQ ID NO: 79) | 9 | | 567 | 317 | 250 | No |
| 8 | 1.07E − 19 | GcCCataGGCCAaCAAcTcTC AGGCTAGACAacGGGCTCTCA (SEQ ID NO: 80) | 9 | Actn1 | 354 | 255 | 99 | No |

Mm: mismatches relative to the intended target site
Frag. A, B: Expected sizes of Surveyor™ nuclease cleavage products
Hit: Rats showing correct Survevor™ nuclease cleavage products As shown, no off-target sites tested showed evidence of modification. As shown, no off-target sites tested showed evidence of modification. Sequencing analysis of CEL-I positive rat #19 shown in FIG. 9A and five of its offspring shown in FIG. 11 at Site 1 revealed that the CEL-I positive signal was due to a SNP near the potential off-target site. The mismatch occurs because the rats are heterozygous for this SNP which was also found in non-treated rats (data not shown). Although present in 50% of chromosomes in CEL-I-positive animals, the SNP is poorly recognized by the CEL-I enzyme resulting in unexpectedly lower-intensity cleavage products.

B. Rab38

ZFNs were also designed to target the endogenous Rab38 locus in rats, particularly exon 1 of the rat Rab38 gene. Exemplary Rab38 zinc-finger designs are shown in Table 8 below.

TABLE 10

Rab38 zinc-finger designs

| ZFN Name | F1 | F2 | F3 | F4 | F5 | F6 |
|---|---|---|---|---|---|---|
| 18160 | DRSNLSS (SEQ ID NO: 81) | RSHSLLR (SEQ ID NO: 82) | RSDSLSA (SEQ ID NO: 38) | TSGSLTR (SEQ ID NO: 25) | QSGNLAR (SEQ ID NO: 21) | QSGHLSR (SEQ ID NO: 83) |
| 18181 | TSGHLSR (SEQ ID NO: 52) | HKWQRNK (SEQ ID NO: 84) | DRSVLRR (SEQ ID NO: 85) | DSSTRKK (SEQ ID NO: 86) | RSDHLSE (SEQ ID NO: 87) | DKSNRKK (SEQ ID NO: 88) |
| 16897 | RSDTLSE (SEQ ID NO: 89) | QKRNRTK (SEQ ID NO: 90) | RSDSLSA (SEQ ID NO: 38) | TSGSLTR (SEQ ID NO: 25) | QSGNLAR (SEQ ID NO: 21) | QSGHLSR (SEQ ID NO: 83) |
| 16898 | RSDHLSK (SEQ ID NO: 91) | HNDSRTN (SEQ ID NO: 92) | DRSDLSR (SEQ ID NO: 28) | RSDHLSE (SEQ ID NO: 87) | DKSNRKK (SEQ ID NO: 88) | N/A |
| 18173 | RSDYLPR (SEQ ID NO: 93) | QSNDLNS (SEQ ID NO: 94) | DRSDLSR (SEQ ID NO: 28) | RSDHLSE (SEQ ID NO: 87) | DKSNRKK (SEQ ID NO: 88) | N/A |
| 18174 | RSDYLPR (SEQ ID NO: 93) | QRVTRDA (SEQ ID NO: 95) | DRSDLSR (SEQ ID NO: 28) | RSDHLSE (SEQ ID NO: 87) | DKSNRKK (SEQ ID NO: 88) | N/A |
| 18175 | HSNARKT (SEQ ID NO: 96) | ASKTRTN (SEQ ID NO: 97) | DRSDLSR (SEQ ID NO: 28) | RSDHLSE (SEQ ID NO: 87) | DKSNRKK (SEQ ID NO: 88) | N/A |
| 18161 | RSHSLLR (SEQ ID NO: 82) | RSDSLSA (SEQ ID NO: 38) | TSGSLTR (SEQ ID NO: 25) | QSGNLAR (SEQ ID NO: 21) | QSGHLSR (SEQ ID NO: 83) | N/A |
| 18183 | RSHSLLR (SEQ ID NO: 82) | RSDYLPR (SEQ ID NO: 93) | DRSVLRR (SEQ ID NO: 85) | DSSTRKK (SEQ ID NO: 86) | RSDHLSE (SEQ ID NO: 87) | DKSNRKK (SEQ ID NO: 88) |

Target sites of the rat Rab38-targeted zinc-finger designs are shown below in Table 11. Nucleotides in the target site that are contacted by the ZFP recognition helices are indicated in uppercase letters; non-contacted nucleotides indicated in lowercase.

TABLE 11

Target Sites of Rab38 Zinc-fingers

| ZFN Name | Target Site (5' to 3') |
|---|---|
| 18161 | gaGGAGAAGTTTTGGTGCACgtagcgct (SEQ ID NO: 98) |
| 18181 | acTACCGGGCCACCATTGGTgtggactt (SEQ ID NO: 99) |
| 16897 | gaGGAGAAGTTTTGgTGCACGtagcgct (SEQ ID NO: 98) |
| 16898 | acTACCGGGCCacCATTGGtgtggactt (SEQ ID NO: 99) |
| 18173 | acTACCGGGCCaCCATTGgtgtggactt (SEQ ID NO: 99) |
| 18174 | acTACCGGGCCaCCATTGgtgtggactt (SEQ ID NO: 99) |
| 18175 | acTACCGGGCCACCATTGggtgtggactt (SEQ ID NO: 99) |
| 18160 | gaGGAGAAGTTTTGGTGcacgtagcgct (SEQ ID NO: 98) |
| 18183 | acTACCGGGCCACCaTTGGTGtggactt (SEQ ID NO: 99) |

All Rab38-targeted ZFNs contained the EL/KK Fok I mutations as described in U.S. Patent Publication No. 2008/0131962. ZFN expression was driven by either the CAG or the CMV promoter. ZFN (1 µg each) were transfected into 200,000 C6 cells via Amaxa nucleofection using the solution SF and the Amaxa Shuttle 96-well nucleofector. Cleavage was assayed with the CEL-I Surveyor™ nuclease as described, for example, in U.S. Patent Publication Nos. 20080015164; 20080131962 and 20080159996.

Rab38 ZFN-encoding expression plasmids were linearized with XbaI, phenol chloroform extracted and precipitated. Messenger RNA was in vitro transcribed using the MessageMax™ T7 ARCA-Capped Message Transcription Kit (Epicentre Biotechnologies). The resulting synthesis was purified using the MegaClear Kit™ (Ambion) before resuspension in RNAse-free 0.1×TE (1 mM Tris-Cl pH 8.0, 0.1 mM EDTA), quantitated using a NanoDrop-1000 (Thermo Scientific) and stored at −80° C. until use. Messenger RNAs encoding Rab38 ZFNs were mixed to a final total concentration of 5 ng/µL in 0.1×TE. Embryos were injected with Rab38 ZFNs under constant time and pressure (Pi=65, Pc=20, ti=1.5s) into the cytoplasm and incubated at 37.5° C. and 5% CO2 in KSOM (Millipore) overnight as previously described in Filipiak et al. (2006) *Transgenic Res* 15:673-686 for molecular analysis.

A mutation-enrichment strategy as described in Lloyd et al. ((2005) *Proc Natl Acad Sci USA* 102:2232-2237) was used to detect alterations of the Rab38 target exon in chromosomes of DNA extracted from embryos cultured for 48 hours post injection.

As shown in FIG. 10, and as demonstrated for both the GFP and IgM loci above, multiple mutant Rab38 alleles could be detected in the genomes of as few as 16 two-cell embryos and sequencing revealed deletions at the target site.

Thus, these data confirm that multiple genomic loci are suitable targets for ZFN-mediated genome editing.

Example 4

ZFN Mediated Germline Modifications

IgM-modified rats #19, #46 and #8 as described in Example 3 were mated to a wild-type rat and tail biopsies were taken, genomic DNA isolated and then CEL-I and PCR assays were performed on the nucleic acid purified from the pups.

Figures 11A, 11B:
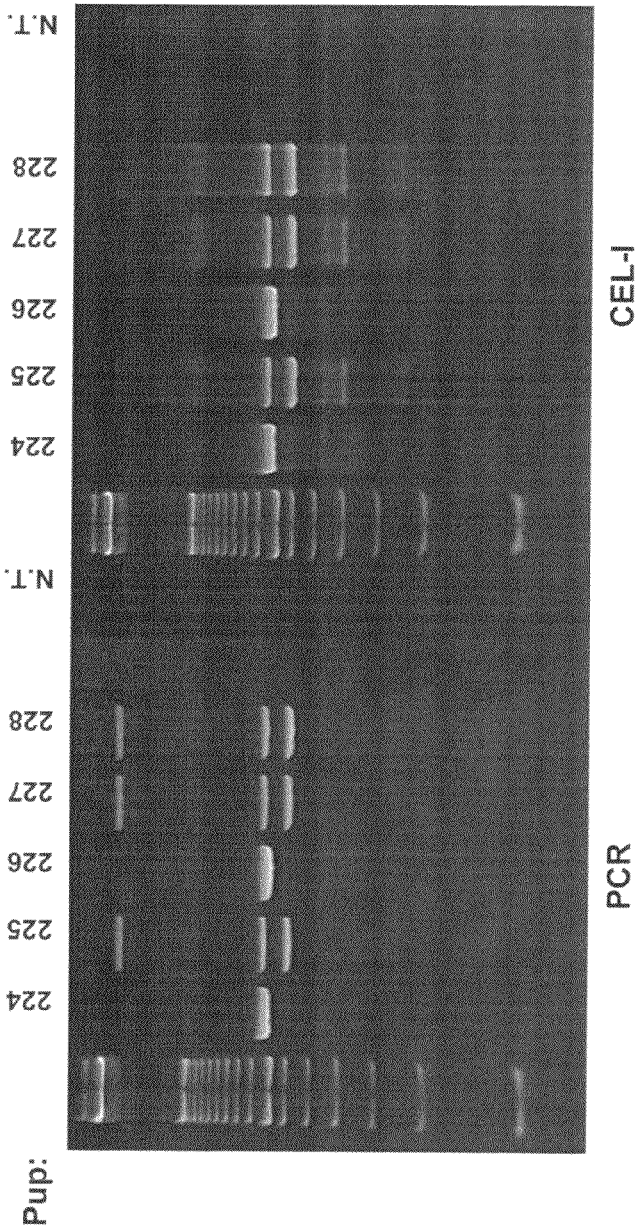
FIG. 11A shows PCR and CEL-I analysis of the 5 pups (numbered 224 to 228) from crossing rat #19 (Example 3) with a wild-type rat.
FIG. 11B (SEQ ID NOS: 172-179) shows sequencing analysis confirmation that the 3 IgM modified pups (#225, 227 and 228 as identified in the figure) include the same 64 basepair deletion allele at the IgM locus as parent rat #19.
Figure 11C:
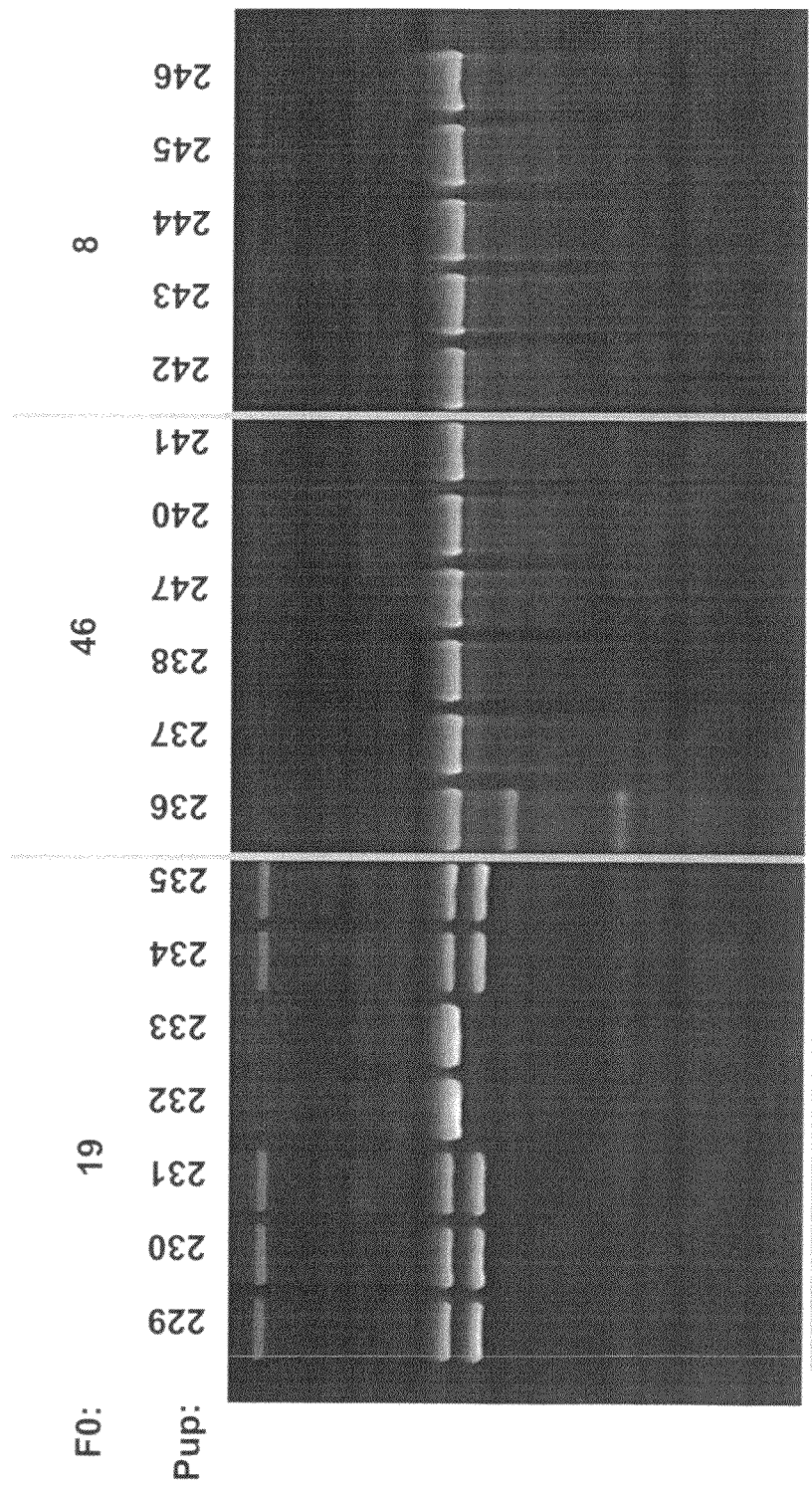
FIG. 11C shows PCR and CEL-I analysis of additions pups of rat #19 as well as pups from crosses of IgM modified rats #46 and #8. The parental IgM-modified rat is indicated at the top "F0" and the numbers of the pups are indicated above each lane.

As shown in FIGS. 11A and 11C, pups (numbered 225, 227, 228, 229, 230, 231, 234 and 235) resulting from a cross between rat #19 and a wild type rat carried the 64 base pair deletion of IgM modified parental rat #19, as determined by PCR and CEL-I assay. In addition, sequencing analysis confirmed that 3 pups of rat #19 (pups #225, 227 and 228) were modified at IgM locus. See, FIG. 11B. Furthermore, as shown in FIG. 11C, a pup resulting from mating rat #46 to a wild-type rat carried the same IgM modification as parental rat #46 (see, pup number 236 of FIG. 11C).

These data demonstrate that ZFN-mediated disruption of a rat locus is transmitted in the germline.

Example 5

Figure 12:
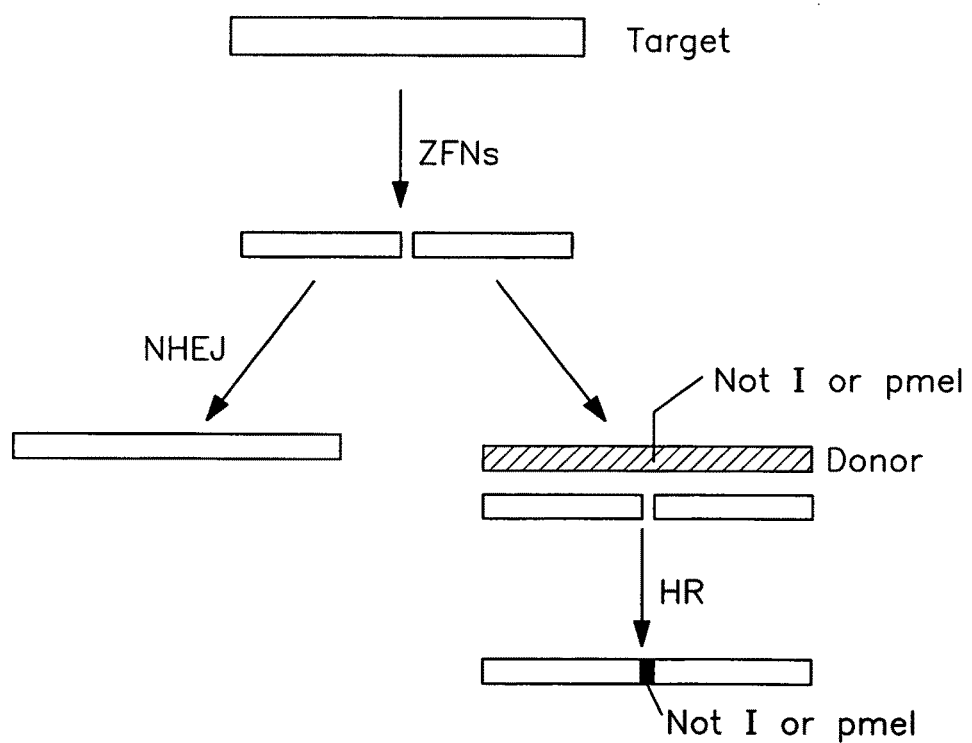
FIG. 12 is a schematic depicting the repair outcomes after a targeted ZFN-induced double stranded break. Shaded bars represent the donor fragment, whereas white bars depict target site for ZFN double stranded break.

Construction of Restriction Fragment Length Polymorphism (RFLP) Donor Nucleic Acid for Targeted Integration into the PXR Nucleic Acid Region of the Rat Genome There are two possible DNA repair outcomes after a targeted, ZFN-induced double-stranded break (FIG. 12). The break may be repaired by non-homologous end joining (NHEJ), leading to mutations containing base deletions or additions or, in the presence of a donor DNA, the donor DNA can be used as a template to repair the double stranded break by homologous recombination (HR). If the donor DNA encodes specific sequence changes, these deliberate mutations will be incorporated into the genome of the organism at the target site.

Figure 13:
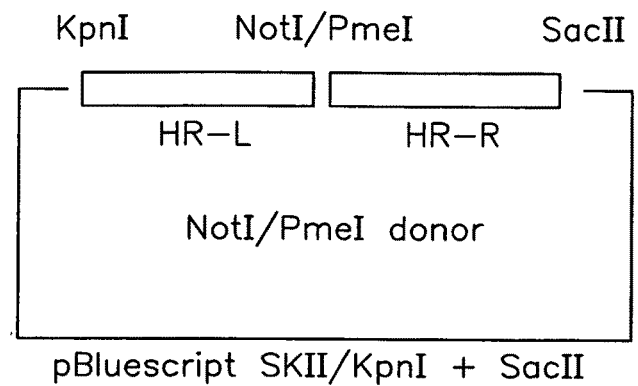
FIG. 13 is a schematic depicting the construction of RFLP donor plasmids. Shown, are the plasmid, and left and right PCR-amplified fragments homologous to the integration target site. Restriction enzymes used for cloning are denoted. The left fragment used KpnI and NotI or PmeI. The right fragment used NotI or PmeI and SacII.

To test targeted integration in the rat genome using pronuclear injection, constructs were designed and prepared for targeted integration into the PXR gene region of the rat genome. Constructs were assembled to introduce either a NotI or PmeI restriction fragment length polymorphism (RFLP) site into the PXR gene region (FIG. 13). The constructs were designed with either 200, 800 or 2000 base pairs of sequence homology to the PXR gene target site flanking the RFLP sites to be introduced. The three sizes of regions of homology were used to determine the size of homology required for efficient targeting and homologous recombination.

The clones were assembled using PCR amplification to introduce convenient restriction sites for cloning, and the RFLP site at the extremities of the PXR homology regions (FIG. 12). PCR primers used for amplifying the PXR region of homology are described in Table 12. Accuprime HF DNA polymerase was used for PCR reaction amplification. A 30s extension was used for the 200 bp fragments, a 1.5 min extension was used for the 800 bp fragments, and a 4 min extension was used for the 2 Kbp fragments. PCR fragments were then digested with the appropriate restriction enzymes and cloned into pBluescript using three-way ligation to produce six plasmids listed in Table 13.

TABLE 12

Primer sequences

| Name | Sequence | |
|---|---|---|
| PXR 200 bp F Kpnl | 5'-aaaaggtacctctgtgtttttccgttctagtccag | (SEQ ID NO: 116) |
| PXR 200 bp R Sacll | 5'-aaaaccgcggctgaagtatacgtggctctcttgga | (SEQ ID NO: 117) |
| PXR target F Notl | 5'-gtgtagcggccgcgacaaggccaatggctatcac | (SEQ ID NO: 118) |
| PXR target F Pmel | 5'-gtgtagtttaaacgacaaggccaatggctatcac | (SEQ ID NO: 119) |
| PXR target R Notl | 5'-ttgtcgcggccgctacacggcagatttgaagacctc | (SEQ ID NO: 120) |
| PXR target R Pmel | 5'-ttgtcgtttaaactacacggcagatttgaagacctc | (SEQ ID NO: 121) |
| PXR 800 bp F Kpnl | 5'-aaaaggtacctcagactggtccagattttagamaagggg | (SEQ ID NO: 122) |
| PXR 800 bp R Sacll | 5'-aaaaccgcggataaatctactggttcgccaagctag | (SEQ ID NO: 123) |
| PXR 2 Kb F Kpnl | 5'-aaaaggtaccgaggtagtaggaaatgcacttc | (SEQ ID NO: 124) |
| PXR 2 Kb R Sacll | 5'-aaaaccgcgggaagagaattattgctgacagtc | (SEQ ID NO: 125) |
| PXR 50 bp F | 5'-gagcctatcaacgtagatgagg | (SEQ ID NO: 126) |
| PXR 50 bp R | 5'-cttacatccttcacaggtcatgac | (SEQ ID NO: 127) |

TABLE 13

Plasmids constructed

| RFLP introduced | Length of region of homology |
|---|---|
| NotI | 200 bp |
| NotI | 800 bp |
| NotI | 2 Kbp |
| PmeI | 200 bp |
| PmeI | 800 bp |
| PmeI | 2 Kbp |

Example 6

Construction of Restriction Fragment Length Polymorphism (RFLP) Donor Nucleic Acid for Targeted Integration into the rRosa26 Nucleic Acid Region of the Rat Genome Plasmids were also constructed to target integration of NotI and PmeI RFLP sites into the rRosa26 nucleic acid region of the rat genome. Design and construction of the plasmids was as described in Example 5 above. The PCR primer pairs used for amplifying the rRosa26 region of homology are described in Table 14.

TABLE 14

Primer sequences

| Name | Sequence |
|---|---|
| rRosa26 200 bp F Kpnl | aaaaggtaccgggagtggatgaaggagttg (SEQ ID NO: 128) |
| rRosa26 200 bp R Sacll | aaaaccgcggcggatcacaagcaataat (SEQ ID NO: 129) |
| rRose26 target F Notl | cttcgcggccgcgatctgcaactggagtctttc (SEQ ID NO: 130) |
| rRosa26 target F Pmel | cttcgtttaaacgatctgcaactggagtctttc (SEQ ID NO: 131) |
| rRosa26 target F Notl | gatcgcggccgcgaagaaggggggaagggaatc (SEQ ID NO: 132) |
| rRosa26 target R Pmel | gatcgtttaaacgaagaaggggggaagggaatc (SEQ ID NO: 133) |
| rRosa26 800 bp F Kpnl | aaaaggtaccgcgtgtgaaaacacaaatgg (SEQ ID NO: 134) |
| rRosa26 800 bp R Sacll | aaaaccgcggaaggaaagaggcattcatgg (SEQ ID NO: 135) |
| rRosa26 2 Kb F Kpnl | aaaaggtaccattatggagggaggactgg (SEQ ID NO: 136) |
| rRosa26 2 Kb R Sacll | aaaaccgcggacatgtggcaaacaggaga (SEQ ID NO: 137) |
| rRosa26 50 bp F | tgtcttctgaggaccgccc (SEQ ID NO: 138) |
| rRosa26 50 bp R | ctgcccagaagactcccgc (SEQ ID NO: 139) |

Example 7

Construction of Restriction Fragment Length Polymorphism (RFLP) Donor Nucleic Acid for Targeted Integration into the Mdr1a Nucleic Acid Region of the Mouse or Rat Genome Plasmids were constructed to target integration of NotI and PmeI RFLP sites into the mMdr1a nucleic acid region of the mouse genome or the rMdr1a nucleic acid region of the rat genome. Design and construction of the plasmids was as described in Example 5 above. The PCR primer pairs used for amplifying the Mdr1a region of homology are described in Tables 15 and 16. "m" stands for mouse and "r" stands for rat.

TABLE 15

| Name | Sequence |
|---|---|
| mMdr1a 200 bp F Kpn1 | aaaaggraccaacaacactaggctcaggag (SEQ ID NO: 140) |
| mMdr1a 200 bp R Sac11 | aaaaccgcggcacatggctaagcacagcatg (SEQ ID NO: 141) |
| mMdr1a target F Not1 | cctgcggccgcggactgtcagctggtatttg (SEQ ID NO: 142) |
| mMdr1a target F Pme1 | cctgtttaaacggactgtcagctggtatttg (SEQ ID NO: 143) |
| mMdr1a target R Not1 | gtccgcggccgcagggctgatggccaaaatc (SEQ ID NO: 144) |
| mMdr1a target R Pme1 | gtccgtttaaacagggctgatggccaaaatc (SEQ ID NO: 145) |
| mMdr1a 800 bp F Kpn1 | aaaaggtaccatgctgtgaagcagatacc (SEQ ID NO: 146) |
| mMdr1a 800 bp R Sac11 | aaaaccgcggctgaaaactgaatgagacatttgc (SEQ ID NO: 147) |
| mMdr1a 2 KB F Kpn1 | aaaaggtaccgtaatgttccaattgcatcttcc (SEQ ID NO: 148) |
| mMdr1a 2 KB R Sac11 | aaaaccgcggctctcagttctctgctgttg (SEQ ID NO: 149) |
| mMdr1a 50 bp F | gatttacccgtggctggaag (SEQ ID NO: 150) |
| mMdr1a 50 bp R | ctggactcatggacttcacc (SEQ ID NO: 151) |

TABLE 15

| Name | Sequence |
|---|---|
| rMdr1a 200 bp F Kpn1 | aaaaggtacctggctcaggagaaaaattgtg (SEQ ID NO: 152) |
| rMdr1a 200 bp R Sac11 | aaaaccgcggcacggctaaagacagcatga (SEQ ID NO: 153) |
| rMdr1a target F Not1 | ccctgcggccgcggactgtcagctggtatttg (SEQ ID NO: 154) |
| rMdr1a target F Pme1 | ccctgtttaaacggactgtcagctggtatttg (SEQ ID NO: 155) |
| rMdr1a target R Not1 | gtccgcggccgcagggctgatggccaaaatc (SEQ ID NO: 156) |
| rMdr1a target R Pme1 | gtccgtttaaacagggctgatggccaaaatc (SEQ ID NO: 157) |
| rMdr1a 800 bp F Kpn1 | aaaaggtaccggagataggctggtttgacg (SEQ ID NO: 158) |
| rMdr1a 700 b R Sac11 | aaaaccgcggatggtggtagttcggatgg (SEQ ID NO: 159) |
| rMdr1a 2 Kb F Kpn1 | aaaaaggtaccaggttgttcttggagatgtgc (SEQ ID NO: 160) |
| rMdr1a 2 Kb T Sac11 | aaaaccgcggtcctcttggctggtgagttt (SEQ ID NO: 161) |
| rMdr1a 50 bp F | gatttactcgcggctggaag (SEQ ID NO: 162) |

TABLE 15-continued

| Name | Sequence |
|---|---|
| rMdr1a 50 bp R | ctggactcacgggcttcac (SEQ ID NO: 163) |

Example 8

Construction of GFP Expression Integration Cassette

Figure 14:
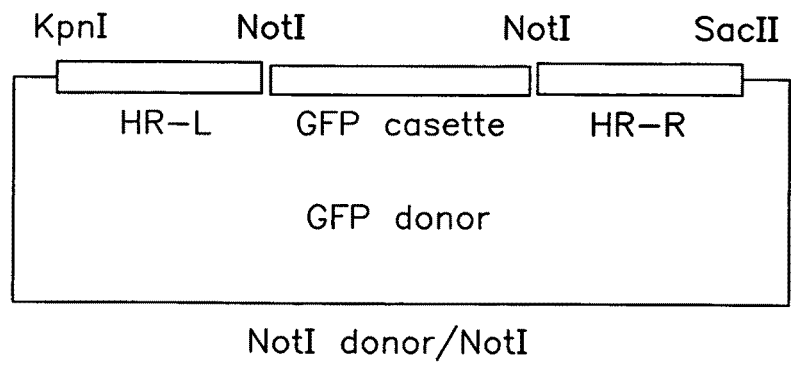
FIG. 14 is a schematic depicting the construction of GFP-expressing donor plasmids. The GFP cassette was PCR amplified from an existing plasmid and closed into the NotI RFLP donor using a NotI site.

To test targeted integration of nucleic acid fragments larger than RFLPs, constructs were designed and prepared for targeted integration of a GFP expression cassette into the PXR and rRosa26 nucleic acid genomic regions of the rat and the mMdr1a nucleic acid genomic regions of the mouse. Briefly, a GFP expression cassette containing the human PGK promoter, the GFP open reading frame, and a polyadenylation signal was amplified using PCR to introduce NotI restriction sites at the extremities (FIG. 14) using the following primers: PGKGFP-F NotI (5'-aaagcggccgcttggggttgcgccttttcc) (SEQ ID NO:164) and PGKGFP-R NotI (5'-aaaagcggccgccata-gagcccaccgcatc) (SEQ ID NO:165). The PCR fragment was then cloned into the NotI-containing plasmids constructed in Examples 5-7.

Example 9

Preparation of Zinc Finger mRNAs for Targeted Integration

A pair of zinc finger nucleases were designed for each targeted integration site and cloned as described on the Sigma web site. For more information, see Science (2009) 325:433, herein incorporated by reference. ZFN expressing mRNAs were then produced in vitro by first digesting 20 µg of each maxiprepped ZFN expression plasmid DNA in 100 µl reactions containing 10 µl buffer 2 (NEB, #B7002S), 10 µl 10×BSA (diluted from 100×BSA, NEB, #B9001S), 8 µl XbaI (NEB, #R0145S), at 37° C. for 2 h. The reactions were extracted with 100 µl of phenol/chloroform (Sigma, P2069), centrifuged at over 20,000×g for 10 min. The aqueous supernatant was precipitated with 10 µl 3M NaOAc (Sigma, 57899) and 250 µl 100% ethanol and centrifuged at top speed for 25 min at room temperature. The resulting pellet was washed by adding 300 µl 70% ethanol filtered through a 0.02 µM filter. The pellet was air dried and resuspended in 20 µl of 0.02 µM filtered 0.1×TE.

The purified digested DNA was then used to produce ZFN transcripts using in vitro transcription with MessageMax T7 Capped Message Transcription Kit (#MMA60710) from Epicentre Biotechnologies as described. In short, kit components are prewarmed to room temperature, and reaction components for a 20 µl reaction were combined at room temperature in the following order: 5 µl of 0.02 um filtered RNase-free water, 1 µl prepared template, 2 µl 1ox transcription buffer, 8 µl 2-way Cap/NTP premix, 2 µl 100 mM DTT and 2 µl MessageMax T7 Enzyme Solution. The reactions were then incubated in a 37° C. incubator for 30 min.

The capped RNA was then tailed with polyA using the A-Plus Poly (A) Polymerase tailing kit (Epicentre, #PAP5 104H) as described. Reaction components were combined at room temperature in the following given order: 55.5 µl 0.02 um filtered RNase-free water, 10 µl 10× A-Plus Reaction Buffer, 10 ul 10 mM ATP, 2.5 µl ScriptGuard RNase Inhibitor (40 unit/µl), 20 µl In vitro transcription capping reaction, 2 µl A-plus poly A polymerase. The reaction was then incubated at 37° C. for 30 min. The resulting capped polyA-tailed mRNA was purified by precipitation with an equal volume of 5M NH$_4$Oac twice. The mRNA pellet was then air dried, and resuspended in 30 µl of filtered injection buffer (1 mM Tris, pH7.4, 0.25 mM EDTA), and RNA concentration was measured using a Nanodrop spectrophotometer.

Example 10

Targeted Integration into Embryos

To integrate nucleic acids into the rat or mouse genome, zinc finger nuclease mRNA was mixed with the maxiprepped target DNA filtered with 0.02 um filters. The nucleic acid mixture consisted of one part ZFN mRNAs to one part donor DNA. The nucleic acid mixture was then microinjected into the pronucleus of a one-celled embryo using known methods. The injected embryos were either incubated in vitro, or transferred to pseudo moms. The resulting embryos/fetus, or the toe/tail of clip live born animals were harvested for DNA extraction and analysis.

Figure 15A:
FIG. 15A is a schematic depicting methods of detecting RFLP integration and restriction enzyme digestion.
Figure 15B:
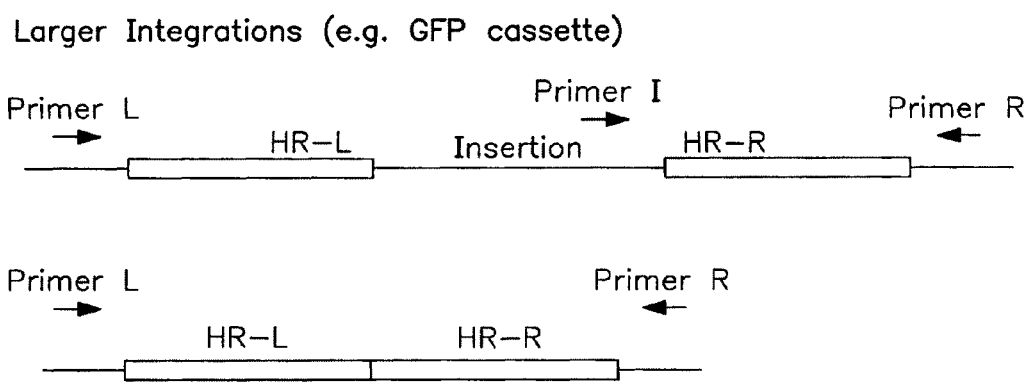
FIG. 15B is a schematic depicting integration of the GFP expression cassette using PCR amplification.

To extract DNA, tissue was lysed in 100 µl Epicentre's QuickExtract at 50° C. for 30 min, followed by incubation at 65° C. for 10 min, and 98° C. for 3 min. To determine if targeted integration occurred, PCR was used to amplify the target region using appropriate primers. For experiments where RFLP was integrated into the genome of the animal, the PCR products were digested with the introduced RFLP enzyme to detect integration (FIG. 15A). In addition, a Cel-I endonuclease assay using wild type PCR fragments and PCR fragments derived from injected embryos was used demonstrate ZFN mRNA was functional in the embryos by detecing NHEJ, which is independent of targeted integration. For experiments where GFP was integrated into the genome of the animal, a shift in size of the PCR fragment is indicative of the integration (FIG. 15B). Alternatively, amplification of the integration junction, where one primer lands only on the GFP cassette was used to assess integration of the donor nucleic acid.

Example 11

Figure 16:
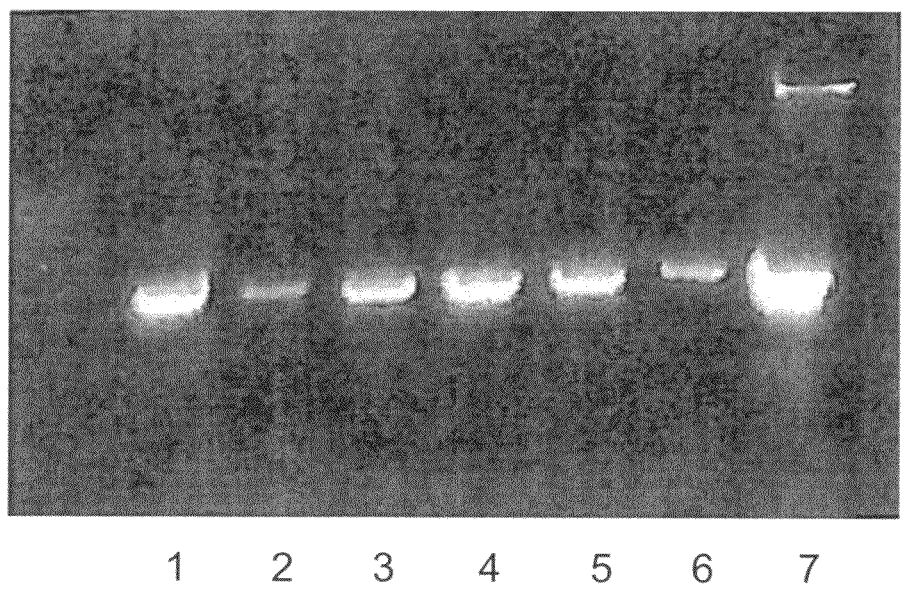
FIG. 16 is a photographic image of fluorescently stained PCR fragments resolved on an agarose gel. The leftmost lane contains a DNA ladder. Lanes 1 to 6 contain PCR fragments amplified using mouse Mdr1a-specific primers from a whole or a fraction of a mouse blastocyst. Lanes 1 and 2 were amplified from ⅚ and ⅙ of a blastocyst, respectively. Lane 3 was from one whole blastocyst. Lanes 4 to 6 were from ½, ⅓, and ⅙ of the same blastocyst, respective. Lane 7 contains a positive control PCR fragment amplified using the same primers from extracted mouse toe DNA.

Testing of DNA Extraction and PCR Amplification of the mMdr1a Target Site in the Mouse Genome PCR conditions to amplify target nucleic acid extracted from tissue were tested using embryos with 1-64 cells extracted as described in Example 10. A 900 bp fragment containing the mouse mMdr1a target region was amplified using 36 amplification cycles with 4 min extension at 60° C. in reactions containing up to 5 µl Epicentre's QuickExtract solution in 50 µl reactions (FIG. 16). These results show that QuickExtract does not interfere with PCR amplification, and that DNA can be amplified from sample extracted from only 1-10 cells. To enhance sensitivity, the number of PCR cycles may be increased, or nested PCR reactions may be performed.

Example 12

Integration of NotI Donor RFLP into the Rat PXR Genomic Region

Figure 17A:
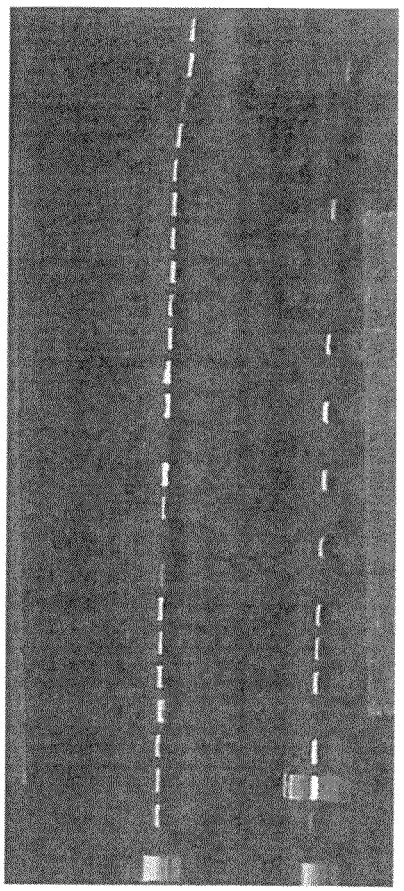
FIG. 17, panels A and B, depict photographic images of fluorescently stained DNA fragments resolved on an agarose gel. The leftmost lanes contain a DNA ladder. Lanes 1 to 39 of FIG. 17A contain PCR fragments amplified using mMdr1a-specific primers from 37 mouse embryos cultured in vitro after being microinjected with ZFN RNA against mouse Mdr1a and RFLP donor with NotI site, along with one positive and negative control for PCR amplification. Lanes 1 to 39 of FIG. 17B contain the PCR fragments of FIG. 17A after performing the Surveyor™ mutation detection assay.
Figure 17B:
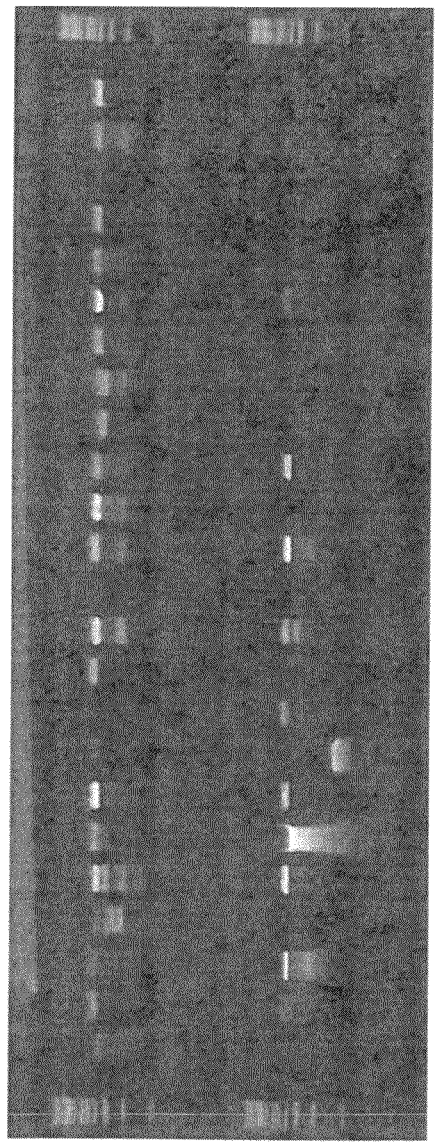

A donor plasmid (with an 800 bp arm) for integrating a NotI RFLP site into the PXR region of the rat genome was injected into rat embryos with ZFN mRNAs as described above. PCR, followed by NotI restriction enzyme analysis and Cel-I endonuclease analysis were performed using DNA extracted from a number of embryos. PCR amplification was successful with a number of embryos (FIG. 17A), and Cel-I endonuclease analysis revealed that most of the fragments had nucleic acid sequence changes at the desired target (FIG. 17B).

Example 13

Integration of NotI Donor RFLP into the Mouse mMdr1a Genomic Region

Figure 18A:
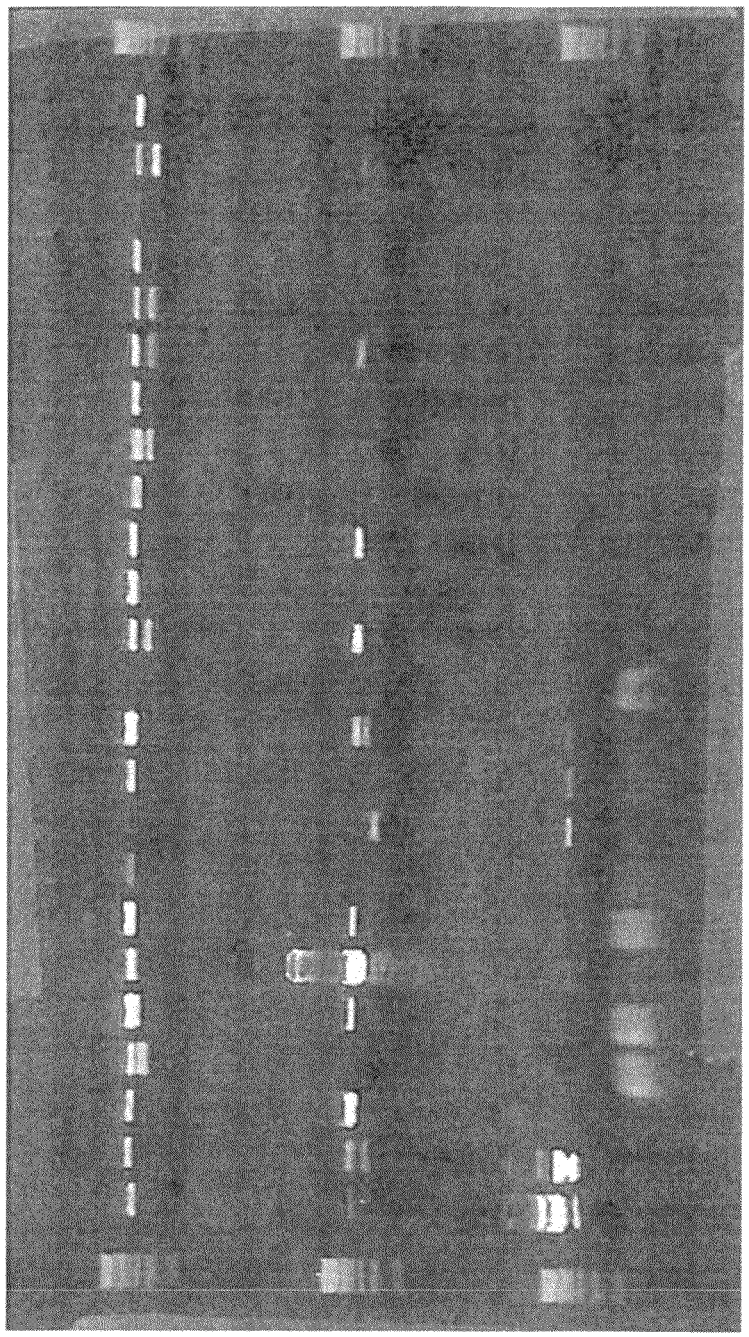
FIG. 18, panels A and B, are photographic images of fluorescently stained DNA fragments resolved on an agarose gel. The leftmost and rightmost lanes contain a DNA ladder. Lanes contain PCR fragments amplified using mMdr1a-specific primers from mouse embryos shown in FIG. 17, and digested with NotI without purifying the PCR product.
FIG. 18B is a longer run of the same gel in FIG. 18A. The uncut PCR products are around 1.8 kb, and the digested products are two bands around 900 bp.

The targeted integration of the NotI RFLP into the mouse mMdr1a region was repeated as described in Example 8. The mMdr1a region was amplified using PCR and digested with NotI. PCR amplification was successful with a number of embryos (FIG. 18), and digestion with NotI revealed that a number of embryos comprised the integrated RFLP site (see e.g. lanes 13, 17, 19, 20 and 23). In all, targeted integration in 7 out of the 32 embryos for which data was generated.

Figure 19:
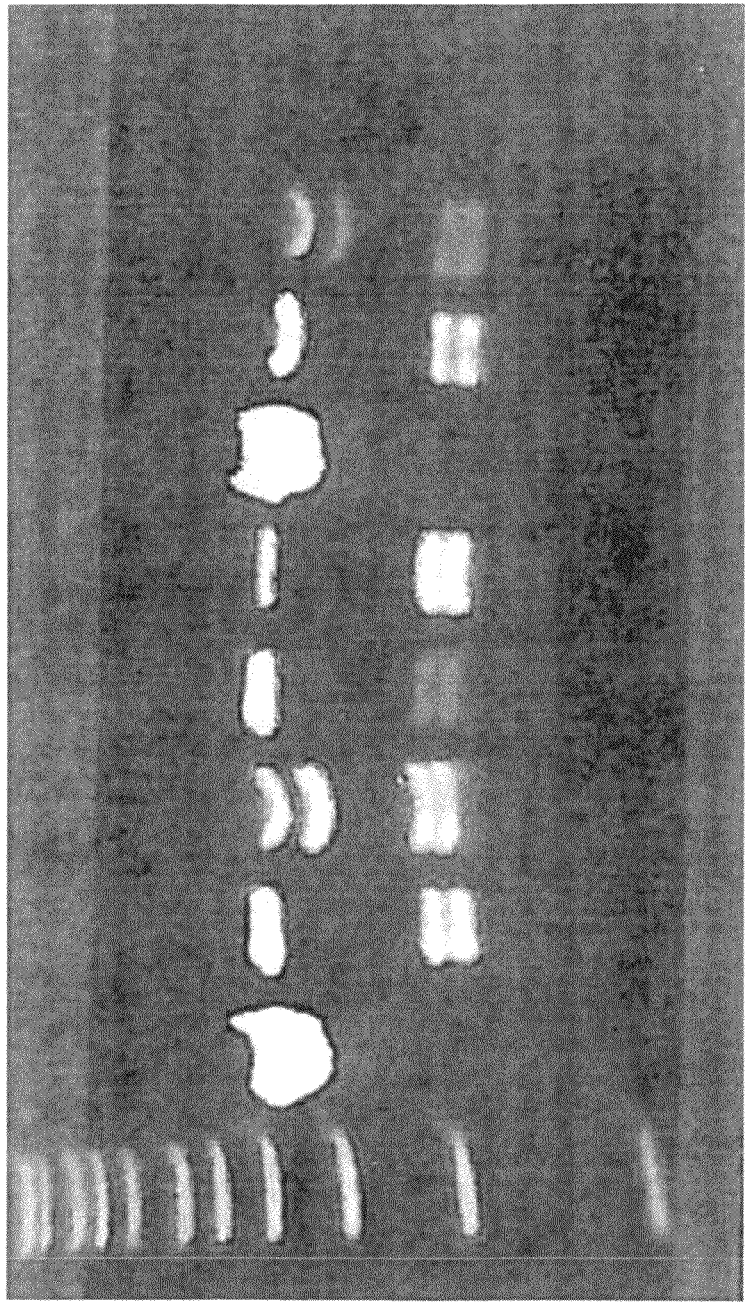
FIG. 19 is a photographic image of fluorescently stained DNA fragments resolved on an agarose gel. The leftmost lane contains a DNA ladder. Lanes 1 to 6 contain some of the PCR fragments from as shown in FIG. 18 digested with NotI after the PCR products were column purified so that NotI can work in its optimal buffer. Lines 7 and 8 are two of the samples digested with NotI (as in FIG. 18). This gel shows NotI digestion in PCR reactions was complete.

These results were confirmed by repeating the NotI digestion reaction after further cleaning the PCR reaction product (FIG. 19).

Example 14

Figure 20:
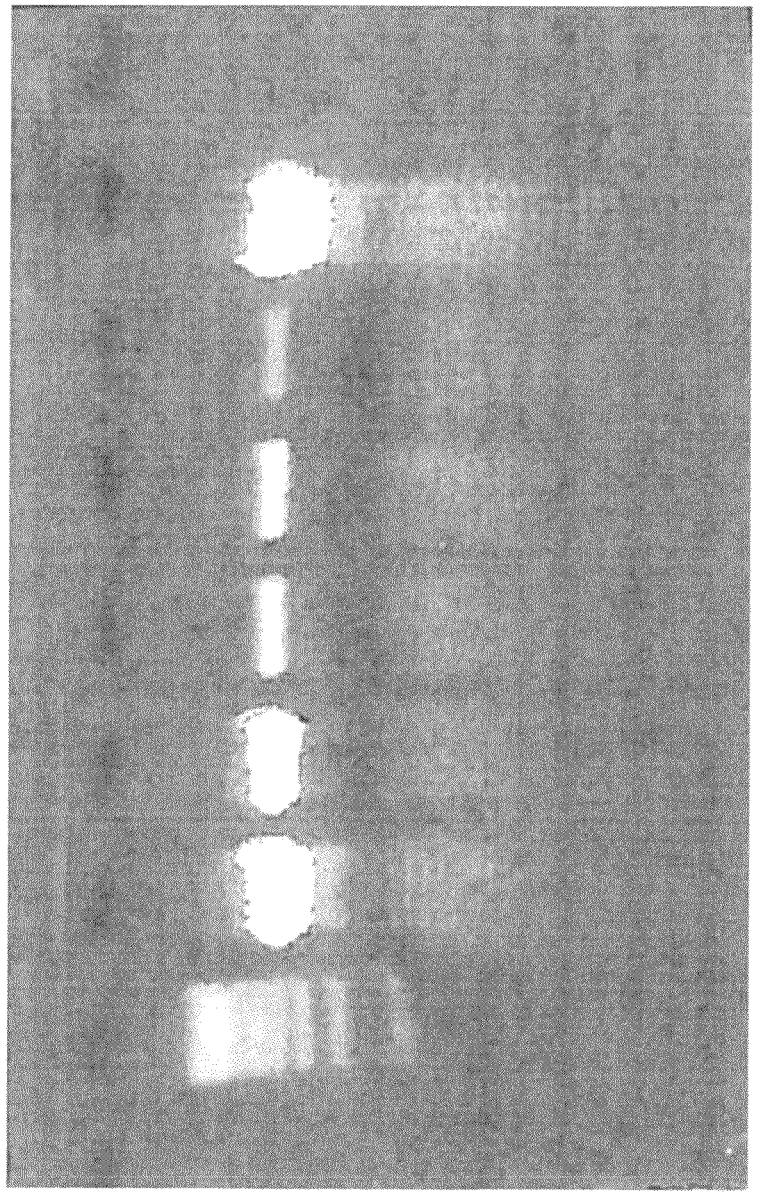
FIG. 20 is a photographic image of fluorescently stained PCR fragments resolved on an agarose gel. The leftmost lane contains a DNA ladder. Lanes 1 to 5 contain PCR fragments amplified using PXR-specific primers from 1, ½, ⅙, 1/10, 1/30 of a rat blastocyst. Lane 6 is a positive control amplified using the same primers from purified Sprague Dawley genomic DNA.

Testing DNA Extraction and PCR Amplification of the PXR Target Site in the Rat Genome PCR amplification of the PXR region from blastocysts was tested to determine the level of sensitivity. The PCR reaction contained 5 µl template, 5 µl PCR buffer, 5 µl of each primer, 0.5 µl of Taq polymerase enzyme, and 33.5 µl water for a 50 µl reaction. The template consisted of undiluted DNA extracted from rat blastocysts or DNA diluted at a ratio of 1:2, 1:6, 1:10, and 1:30 (FIG. 20).

Example 15

Integration of NotI Donor RFLP into the Rat PXR Genomic Region

A donor plasmid (with 800 bp homology arms) for integrating a NotI RFLP site into the PXR region of the rat genome was injected into rat embryos with ZFN mRNAs as described above. A total of 123 embryos were injected, and 106 survived. Decreasing concentrations of nucleic acids were injected to test for toxicity. Of the 51 embryos injected with 5 ng of nucleic acids, 17 survived and divided to two cell embryos on day two. Of the 23 embryos injected with 2 ng of nucleic acids, 14 survived and divided to two cell embryos on day two. Of the 29 embryos injected with 10 ng of nucleic acids, 12 survived and divided to two cell embryos on day two. Of the ten uninjected control embryos, all survived and divided to two cell embryos on day two.

Figure 21A:
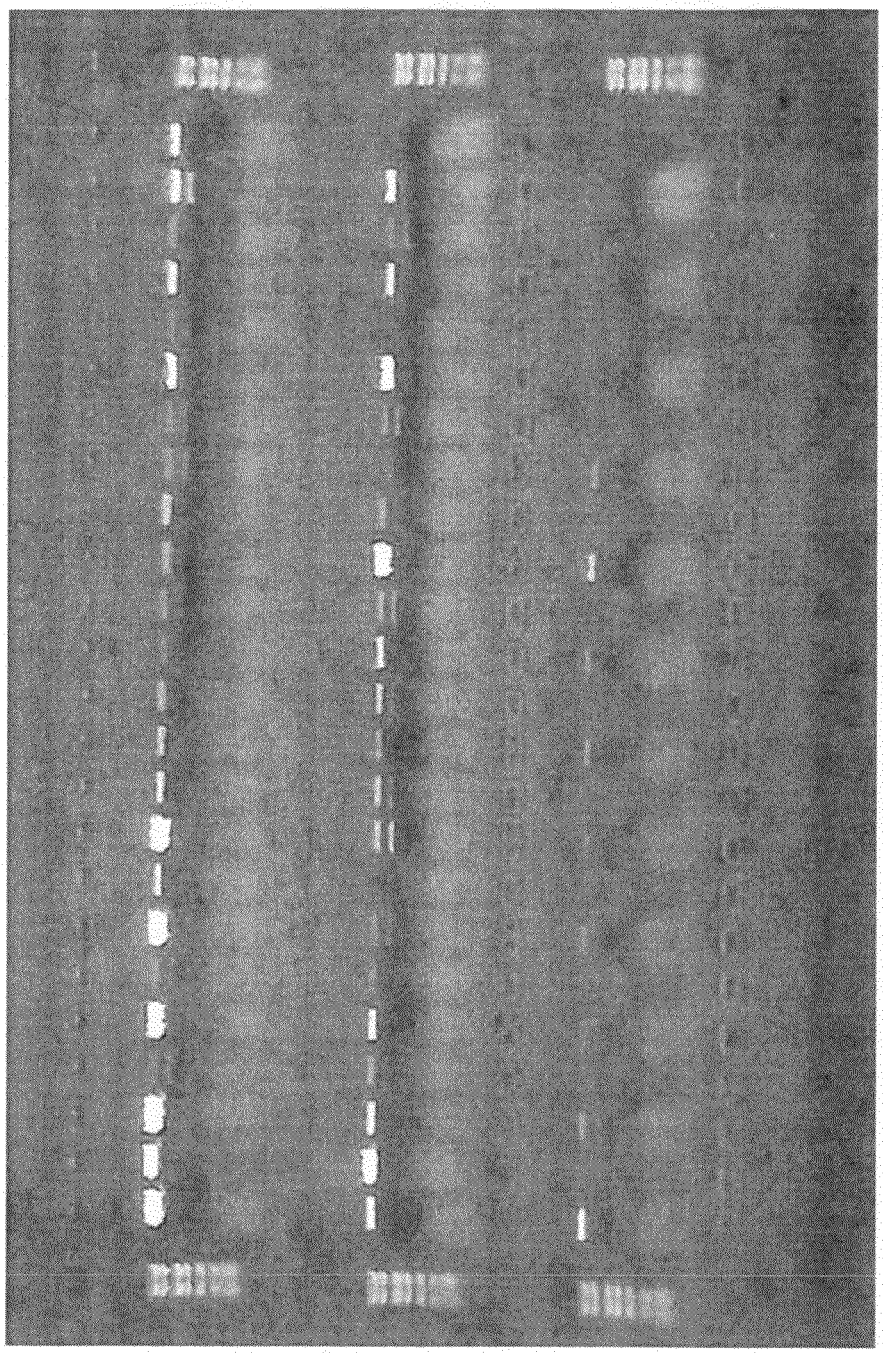
FIG. 21A shows PCR fragments amplified from rat embryos cultured in vitro after microinjection of PXR ZFN mRNA and the NotI RFLP donor, using PXR-specific primers and digested with NotI.
Figure 21B:
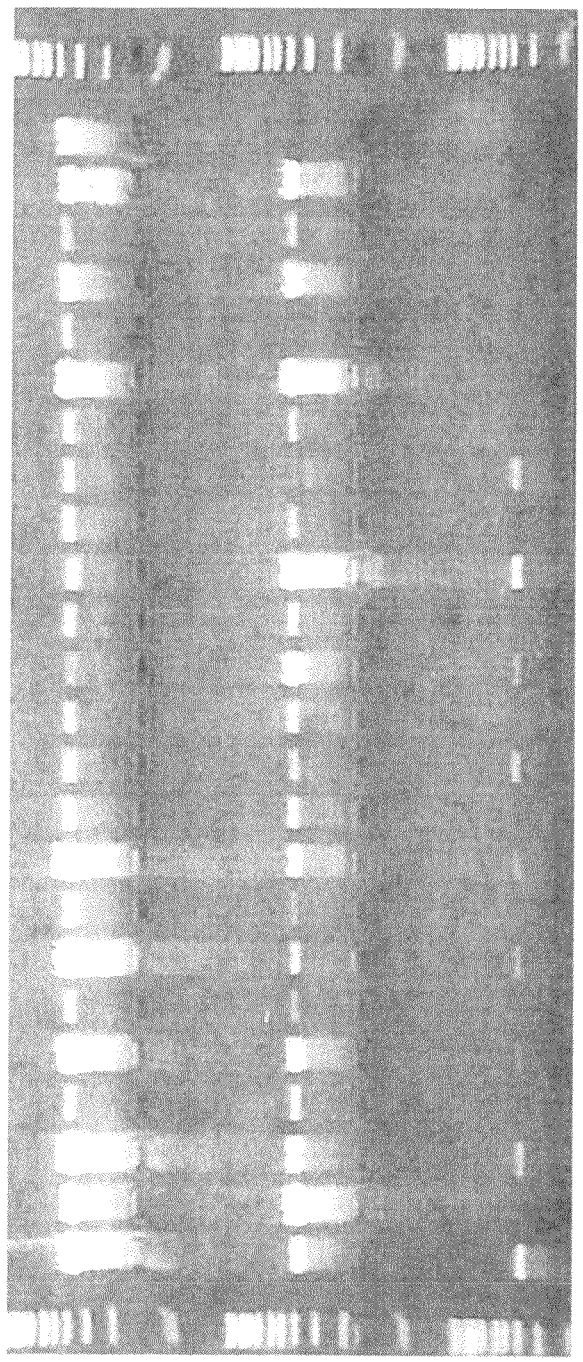
FIG. 21B shows the same PCR fragments as in FIG. 21A after performing the Surveyor™ mutation detection assay.

PCR amplification of the PXR region, followed by NotI and Cel-I endonuclease analysis were performed using DNA extracted from a number of embryos. PCR amplification was successful with a number of embryos, and NotI and Cel-I endonuclease analysis revealed that 18 out of 47 embryos had nucleic acid sequence changes at the desired target (FIG. 21).

Example 16

Figure 22:
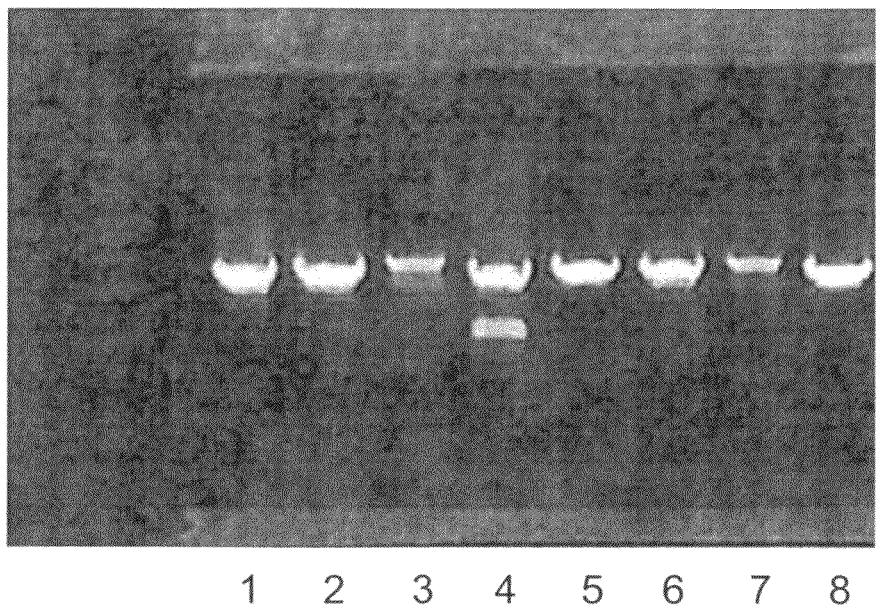
FIG. 22 is a photographic image of fluorescently stained DNA fragments resolved on an agarose gel. The first 4 lanes are PCR amplified from 4 well developed fetus at 12.5 days post conception from embryos injected with mMdr1a ZFN mRNA with the NotI RFLP donor. The PCR was digested with NotI. Lane 4 is positive one. Lanes 5-8 are 4 decidua, aborted implantations. All four were negative.

Targeted Integration of RFLP into the mMdr1a Target Region of the Mouse Genome in Fetus A donor plasmid (with 800 bp homology arms) for introducing NotI into the mMdr1a region of the mouse genome was injected into mouse embryos with ZFN mRNAs as described above. One out of four well-developed fetuses at 12.5 dpc were positive for the NotI site. All four deciduas were negative: (FIG. 22).

Example 17

Targeted Integration of GFP into the mMdr1a Locus of a Fetus

A donor plasmid (with 800 bp homology arms) for introducing GFP cassette into the mMdr1a region of the mouse genome was injected into mouse embryos with ZFN mRNAs as described above. Two out of forty fetuses at 12.5 dpc were positive for the GFP cassette (FIG. 23).

Example 18

Figure 24:
FIG. 24 is a photographic image of DNA fragments resolved on an agarose gel. Lane 8 represents a 13 dpc fetus positive for the NotI site.

Targeted Integration of RFLP into the PXR Target Region of the Rat Genome in a Fetus A donor plasmid (with 800 bp homology arms) for introducing NotI into the PXR region of the rat genome was injected into mouse embryos with ZFN mRNAs as described above. One out of eight fetuses at 13 dpc were positive for the NotI site (FIG. 24).

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

---

What is claimed is:

1. A method for making a deletion in an endogenous IgM gene, the method comprising:
introducing mRNA into an isolated rat cell, wherein the mRNA comprises
(i) mRNAs encoding a first zinc finger nuclease (ZFN) that binds to a first target site in an endogenous rat IgM gene wherein the first ZFN comprises a cleavage domain and a zinc finger protein, wherein the first zinc finger protein-comprises the following recognition helices in the following order:
DRSHLTR (SEQ ID NO:41);
RSDALTQ (SEQ ID NO:40);
DRSDLSR (SEQ ID NO:28);
RSDALAR (SEQ ID NO:39);
RSDSLSA (SEQ ID NO:38); and
TSSNRKT (SEQ ID NO:37), and
(ii) mRNA encoding a second ZFN that binds to a second target site in the endogenous rat IgM gene, wherein the second ZFN comprises a cleavage domain and a zinc finger protein comprising the following recognition helices in the following order:
NKVGLIE (SEQ ID NO:46);
TSSDLSR (SEQ ID NO:45);
RSDHLSR (SEQ ID NO:44);
RSDNLSE (SEQ ID NO:43); and
QNAHRKT(SEQ ID NO:42),
such that the first and second ZFNs are expressed, dimerize and cleave the endogenous rat IgM gene and non-homologous end joining (NHEJ) occurs causing the cell to have a deletion in the endogenous rat IgM gene.

2. The method of claim 1, wherein the cleavage domain is a Type IIS restriction endonuclease cleavage domain.

* * * * *